US005710266A

United States Patent [19]

McKnight et al.

[11] Patent Number: 5,710,266

[45] Date of Patent: Jan. 20, 1998

[54] NUCLEIC ACID ENCODING AN INTERLEUKIN 4 SIGNAL TRANSDUCER

[75] Inventors: Steven L. McKnight; Jinzhao Hou, both of South San Francisco, Calif.

[73] Assignee: Tularik Inc., South San Francisco, Calif.

[21] Appl. No.: 781,890

[22] Filed: Jan. 5, 1997

Related U.S. Application Data

[60] Division of Ser. No. 276,099, Jul. 15, 1994, Pat. No. 5,591,825, which is a continuation-in-part of Ser. No. 269,604, Jul. 5, 1994, abandoned.

[51] Int. Cl.$^6$ .............................. C12N 15/12; C07K 14/47

[52] U.S. Cl. ......................... 536/23.5; 530/350; 536/23.1; 536/24.3; 536/24.31; 435/6

[58] Field of Search .................................. 536/23.1, 23.5, 536/24.3, 24.31; 530/350; 435/6

[56] References Cited

PUBLICATIONS

Darnell Jr. Et al., "Jak–STAT Pathways and Transcriptional Activation in Response to IFNs and Other Extracellular Signaling Proteins", *Science* 264:1415–1421 (1994).

Greenlund et al., "Ligand–induced $IFN_{\gamma}$ Receptor Tyrosine Phosphorylation Couples the Receptor to its Signal Transduction System (p. 91)", *The EMBO Journal* 13(7):1591–1600 (1994).

Hou et al., "An Interleukin–4–induced Transcription Factor: IL–4 Stat", *Science* 265:1701–1706 (1994).

Köhler and Rieber, "Allergy–associated Iε and Fcε Receptor II (CD23b) Genes Activated via Binding of an Interleukin–4–induced Transcription Factor to a Novel Responsive Element", *Eur. J. Immunol.* 23:3066–3071 (1993).

Kotanides and Reich, "Requirement of Tyrosine Phosphorylation for Rapid Activation of a DNA Binding Factor by IL–4", *Science* 262:1265–1267 (1993).

Paul and Seder, "Lymphocyte Responses and Cytokines", *Cell* 76:241–251 (1994).

Schindler et al., "STF–IL–4: A Novel IL–4–induced Signal Transducing Factor", *The EMBO Journal* 13(6):1350–1356 (1994).

Shuai et al., "Activation of Transcription by IFN–$\gamma$: Tyrosine Phosphorylation of a 91–kD DNA Binding Protein", *Science* 258:1808–1812 (1992).

Shuai et al., "Interferon Activation of the Transcription Factor Stat91 Involves Dimerization through SH2–Phosphotyrosyl Peptide Interactions", *Cell* 76:821–828 (1994).

Yin et al., *J. Biol. Chem.* 269:26614–26617 (1994).

*Primary Examiner*—John Ulm
*Assistant Examiner*—Prema Mertz
*Attorney, Agent, or Firm*—Richard Aron Osman

[57] ABSTRACT

The invention provides methods and compositions for identifying pharmacological agents useful in the diagnosis or treatment of disease associated with the expression of a gene modulated by an interleukin 4 signal transducer and activator of transcription, IL-4 Stat. IL-4 Stat peptides and IL-4 receptor peptides and nucleic acids encoding such peptides find therapeutic uses. The subject compositions include IL-4 Stat and IL-4 receptor proteins, portions thereof, nucleic acids encoding them, and specific antibodies. The disclosed pharmaceutical screening methods are particularly suited to high-throughput screening where one or more steps are performed by a computer controlled electromechanical robot comprising an axial rotatable arm.

3 Claims, No Drawings

NUCLEIC ACID ENCODING AN INTERLEUKIN 4 SIGNAL TRANSDUCER

CROSS-REFERENCE TO RELATED APPLICATIONS

This is a divisional of U.S. patent application Ser. No. 08/276,099, filed 15 Jul. 1994, now U.S. Pat. No. 5,591,825, which is a continuation-in-part of U.S. patent application Ser. No. 08/269,604, filed 5, Jul. 1994, now abandoned.

FIELD OF THE INVENTION

The field of this invention is interleukin 4 signal transducers.

BACKGROUND

Identifying and developing new pharmaceuticals is a multibillion dollar industry in the U.S. alone. Gene specific transcription factors provide a promising class of targets for novel therapeutics directed to these and other human diseases. Urgently needed are efficient methods of identifying pharmacological agents or drugs which are active at the level of gene transcription. If amenable to automated, cost-effective, high throughput drug screening, such methods would have immediate application in a broad range of domestic and international pharmaceutical and biotechnology drag development programs.

Immunosuppression is therapeutically desirable in a wide variety of circumstances including transplantation, allergy and other forms of hypersensitivity, autoimmunity, etc. Cyclosporin, a widely used drag for effecting immunosuppression, is believed to act by inhibiting a calcineurin, a phosphatase which activates certain transcription factors. However, because of side effects and toxicity, clinical indications of cyclosporin (and the more recently developed FK506) are limited.

Interleukin-4 (IL-4) is an immunomodulatory cytokine secreted by activated T lymphocytes, basophils and mast cells. IL-4 plays an important role in modulating the balance of T helper cell subsets, favoring expansion of the Th2 lineage relative to TH1 . Imbalance of these T lymphocyte subsets has been implicated in immunological diseases including allergy, inflammation and autoimmune disease. Accordingly, it is desired to identify agents which specifically interfere with transduction of IL-4 signalling. Unfortunately, the reagents necessary for the development of high-throughput screening assays for such therapeutics are unavailable.

Relevant Literature

For recent reviews, see W. E. Paul and R. A. Seder (1994) Cell 76, 241–251 and Darnell et al. (1994) Science 264, 1415. More specific references include: Shuai et at. (1992) Science 258, 1808–1812; Kotanides and Reich (1993) Science 262, 1265–1267; Schindler et al. (1994) The EMBO J 13, 1350–1356; Ingrid Kohler and E. P. Rieber (1993) Eur J Immunol 23, 3066–3071. For recent work relating to the IFN-g receptor and p91, see Shuai et at., (1994) and Greenlund et al., (1994) The EMBO J 13, 4604–4610. See also copending U.S. applications Ser. Nos. 08/246,977 and 08/046,585.

SUMMARY OF THE INVENTION

The invention provides methods and compositions for identifying pharmacological agents useful in the diagnosis or treatment of disease associated with the expression of one or more genes modulated by a transcription complex containing an interleukin signal transducer and activator of transcription, IL-4 Stat. The invention also provides methods and composition useful in diagnosis and therapy for disease associated with undesirable cell growth, differentiation and/or cytokine signal responsiveness.

The invention provides recombinant human IL-4 Stat peptides capable of selectively binding binding targets of IL4 Stat. Such binding targets are or derive from natural intracellular binding targets and include transcription factors, enzymes such as a phosphatases or kinases, cellular receptors such as the IL4 receptor and nucleic acids, such as nucleic acids encoding one or more IL-4 Stat binding sequences. Nucleic acid encoding the subject IL-4 Stat portions, vectors and cells comprising such nucleic acids are used to as probes for IL-4 Stat homologs and/or for recombinantly producing IL-4 Stat peptides. The invention also provides IL-4 Stat binding targets such as cytokine receptor peptides; in particular, IL-4 receptor peptides which selectively bind IL-4 Stat peptides, nucleic acids encoding such receptor peptides, and binding reagents, such as antibodies selective for such peptides or for IL-4 Stat peptides.

In one embodiment, the invention provides methods of identifying a pharmacological agent useful in the diagnosis or treatment of disease associated with the expression of an IL-4 Stat-modulated gene. In general, the methods involve combining a IL-4 Stat peptide capable of selectively binding a natural cellular binding target of the IL-4 Stat with at least a portion, fragment or structural analog of a natural cellular target of the IL-4 Stat that is sufficient to selectively bind the IL-4 Stat, and a candidate pharmacological agent. The resultant mixture is incubated under conditions whereby, but for the presence of the candidate pharmacological agent, the IL-4 Stat peptide selectively binds the binding target. Then the presence or absence of selective binding between the IL-4 Stat peptide and the binding target is detected; where the absence of selective binding indicates that the candidate pharmacological agent is capable of selectively interfering with IL-4 Stat modulated function, such as gene expression. Such an agent is useful in the diagnosis or treatment of disease, particularly immune disease, associated with the expression of the gene.

A wide variety of alternative embodiments of the general methods using IL-4 Stat and IL-4 receptor peptides are disclosed. These encompass a variety of genes, transcription factors and methods for isolating and detecting polypeptides and transcription complexes, e.g. ligand tagging followed by immobilized receptor isolation, direct labels, specific binding labels, etc. The methods are particularly suited to high-throughput screening where one or more steps are performed by a computer controlled electromechanical robot comprising an axial rotatable arm and the solid substrate is a portion of a well of a microtiter plate.

DETAILED DESCRIPTION OF THE INVENTION

The invention provides methods and compositions relating to IL-4 Stats—a novel family of transcription factors. An IL-4 Stat cDNA and amino acid sequence are disclosed in SEQUENCE ID NOS; 1 and 2, respectively. IL-4 Stats are Characterized by selective binding to intracellular domains of cytokine receptors and nucleic acids encoding IL-4 Stat binding sites such as shown in Table 1. Preferred binding sites include two trinucleotides of the sequences: TTC and GAA, where the trinucleotides are separated by from 1 to 5 nucleotides. IL-4 Stats include SH2 and SH3 domain structures their amino acid sequences share substantial sequence similarity with that of SEQUENCE ID NOS: 2. Preferred IL-4 Stats have cDNAs which share substantial sequence similarity with that of SEQUENCE ID NO: 1. Polypeptides with substantial sequence similarity present at least about 55%, preferably at least about 70%, more preferably at least about 80%, and most preferably at least about 90% sequence identity as determined by pair-wise distance matrix comparisons carried out using the CLUSTAL V protein alignment software distributed by EMBL. Within the SH2 domain the family members are at least about 65%, preferably at least about 75%, more preferably at least about 85%, most preferably at least about 95% identical as determined by pair-wise distance matrix comparisons. Where the sequences diverge, the differences are preferably conservative, i.e. an acidic for an acidic amino acid substitution.

Substantially identical or homologous nucleic acid sequences hybridize to their respective complements under high stringency conditions, for example, at 55° C. and hybridization buffer comprising 50% formamide in 0.9M saline/0.09M sodium titrate (SSC) buffer and-remain bound when subject to washing at 55° C. with the SSC/formamide buffer. Where the sequences diverge, the differences are preferably silent, i.e. or a nucleotide change providing a redundant codon, or conservative, i.e. a nucleotide change providing a conservative amino acid substitution.

The invention provides IL-4 Stat peptides capable of selectively binding at least one natural IL-4 Stat binding target. IL-4 Stat peptides are of length sufficient to provide a novel peptide. As used herein, peptides are at least 5, usually at least about 6, more usually at least about 8, most usually at least about 10 amino acids and up to 50 amino acids in length. Peptides may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc.

The IL-4 Stat peptides are capable of selectively binding at least one natural IL-4 Stat binding target. Exemplary binding targets include cytokine receptors, especially interleukin receptors, especially the IL-4 receptor or receptors with substantial sequence similarity to IL-4 receptors, nucleic acids which comprise one or more IL-4 Stat DNA binding sites, transcription factors including IL-4 Stat itself, etc. Other natural IL-4 Stat binding targets are readily identified by screening cells, membranes and cellular extracts and fractions with the disclosed materials and methods and by other methods known in the art. Binding targets are capable of selectively binding an IL-4 Stat peptide, i.e. with an equilibrium constant at least about $10^4M^{-1}$, preferably at least about $10^6M^{-1}$, more preferably at least about $10^8M^{-1}$ and not less than six, preferably not less than four, more preferably not less than two orders of magnitude less than the binding equilibrium constant of full-length native IL-4 Stat to the binding target under similar conditions.

Preferred peptides include IL-4 Stat amino acid residues sufficient to provide the peptide (or a polypeptide comprising the IL-4 Stat peptide) with binding affinity and specificity similar to that of the native IL-4 Stat. Preferred peptide and target portions capable of imparting the requisite binding specificity and affinity are readily identified by those skilled in the art. A wide variety of molecular and biochemical methods are available for generating preferred portions, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. for example, deletion mutants are screened for selective protein or sequence-specific binding directly using binding assays including those described herein or other assays such as fluorescence resonance energy transfer (FRET) or electrophoretic mobility shift analysis (EMSA).

Also provided are novel agents which selectively bind the subject IL-4 Stat peptides. Included are novel portions of natural cellular binding targets and antibodies. Excluded are natural and known products such as the published full-length IL-4 receptor. However, cytokine receptors, particularly interleukin receptors, particularly the IL-4 receptor is shown herein to contain peptides which selectively bind IL-4 Stat. Thus, the invention provides novel peptides of known proteins (e.g. IL-4 receptor peptides) flanked by other than a naturally flanking amino acid residue. Hence, the peptides may be flanked on one or both sides by one or more amino acid residues not naturally flanking the peptide in the native state or the peptides may terminate in an amino acid residue without a distal peptide bond, i.e. at least one of an N or C terminal residue with not joined to another amino acid. Materials and methods for making such agents (e.g. nucleic acids encoding the IL-4 receptor peptides) are disclosed herein or otherwise known in the art. Methods for making IL-4 Stat peptide- and IL-4 receptor peptide-specific antibodies, including monoclonals, are described in Harlow and Lane, Antibodies: A laboratory Manual, Cold Spring Harbor, 1988.

The invention provides efficient methods of identifying pharmacological agents or drugs which are active at the level of IL-4 Stat and IL-4 receptor modulatable cellular function, particularly gene transcription. The methods are amenable to automated, cost-effective high throughput drag screening and have immediate application in a broad range of domestic and international pharmaceutical and biotechnology drug development programs.

Target therapeutic indications are limited only in that the target cellular function (e.g. gene expression) be subject to inhibition by alteration of the formation of a complex (e.g. transcription complex) comprising the subject IL-4 Stat or IL-4 receptor and/or its specific interaction natural cellular binding targets (e.g. with a gene or gene regulatory region). Since a wide variety of genes are subject to IL-4 Stat or IL-4 receptor-modulated gene transcription, target indications may include viral, bacterial and fungal infections, metabolic disease, genetic disease, cell growth and regulatory disfunction, such as neoplasia, inflammation, hypersensitivity, etc. Frequently, the target indication is an undesirable immune response, for example, in transplantation and transfusion, all types of hypersensitivity including immediate types such as allergies and delayed types, autoimmunity including that induced by vital infection such as HIV.

The invention provides a wide variety of binding and expression assays for compounds which interfere with IL-4 receptor or IL-4 Stat modulated gene transcription. While the following descriptions are directed primarily to IL-4 Stat assays, they are also analogously applicable to IL-4 receptor peptide based assays.

The disruption of IL-4 Stat binding may be detected with a IL-4 Stat peptide (or peptide containing polypeptide) and an IL-4 receptor peptide which binds IL-4 Stat. Either component may be labelled, e.g. with radiolabelled phosphate using HMK and either component may be immobilized, eg. by labeling with biotin and binding to an avidin coated substrate. Alternatively, the disruption of IL-4 Stat IL-4 Stat dimerization or IL-4 Stat—DNA binding may be assayed. IL-4 Stat peptides may be obtained by any convenient way, for example, by chemical synthesis, expression in vaccinia or baculovirus-based expression systems, etc. To obtain active, tyrosine phosphorylated IL-4 Stat, IL-4 Stat can be coexpressed with a JAK kinase. Alternatively, recombinant IL-4 Stat can be treated with an exogenous IL-4 Stat kinase in the form of cellular extracts or purified preparations thereof.

Peptides (or polypeptides containing such peptides) used in the disclosed methods are usually added in an isolated, partially pure or pure form and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample. It is often desirable that the peptide be part of a fusion product with another peptide or polypeptide, e.g. a polypeptide that is capable of providing or enhancing protein-protein binding, sequence-specific nucleic acid binding or stability under assay conditions (e.g. a tag for detection or anchoring).

The assay mixtures comprise at least a portion of a natural cellular IL-4 Stat binding target such as an IL-4 receptor peptide or a nucleic acid comprising a sequence which shares sufficient sequence similarity with a gene or gene regulatory region to which the native IL-4 Stat naturally binds to provide sequence-specific binding of the IL-4 Stat peptide (or peptide-containing polypeptide). The nucleic acid may further comprise one or more sequences which facilitate the binding of a second transcription factor peptide (or peptide containing polypeptide) which cooperatively binds the nucleic acid with the IL-4 Stat peptide (i.e. at least one increases the affinity or specificity of the DNA binding of the other). While native binding targets may be used, it is frequently preferred to use portions (e.g. peptides, nucleic acid fragments) or analogs (i.e. agents which mimic the IL-4 binding properties of the natural binding target for the purposes of the assay) thereof so long as the portion provides binding affinity and avidity to the IL-4 Stat peptide conveniently measurable in the assay.

Binding site portions of the nucleic acid constitute at least about 4, preferably at least about 6, more preferably at least about 8 nucleotides. Nucleic acids comprising an IL-4 Stat binding site include at least a portion of a nucleotide sequence in Table 1, preferably including the sequence TTC—GAA on one strand where TTC and GAA are separated by from 1 to 5 nucleotides.

TABLE 1

| | | | |
|---|---|---|---|
| FcγRI | 5'-GTATTTCCCAGAAAAGGAAC<br>CATAAAGGGTCTTTTCCTTG | (SEQ ID NO: 03) | −33/−14 |
| FcεRIIa | -CTCTTACCTGAGAAATGG | (SEQ ID NO: 04) | −131/−114 |
| FcεRIIb | -GAATTTCTAAGAAAGGG | (SEQ ID NO: 05) | −230/−214 |
| $C_\gamma 1$ | -ACATTCACATGAAGTA | (SEQ ID NO: 06) | −126/−111 |
| $C_\epsilon$ | -AACTTCCCAAGAACAG | (SEQ ID NO: 07) | −119/−104 |
| mMHCIIEβ | -AAGGTTTCAGAAGGG | (SEQ ID NO: 08) | −165/−152 |
| hMHCIIDRα | -CCTTCCCCTAGCAACAG | (SEQ ID NO: 09) | −115/−99 |

Binding sequences for other transcription factors may be found in sources such as the Transcription Factor Database of the National Center for Biotechnology Information at the National Library for Medicine, in Faisst and Meyer (1991) Nucleic Acids Research 20, 3–26, and others known to those skilled in this art.

The nucleic acid potion bound by the peptide(s) may be continuous or segmented. Additional nucleotides may used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors. In addition, the nucleic acid can comprise a cassette into which transcription factor binding sites are conveniently spliced for use in the subject assays.

The nucleic acid is usually linear and double-stranded DNA, though circular plasmids or other nucleic acids or structural analogs may be substituted so long as IL-4 Stat sequence-specific binding is retained. In some applications, supercoiled DNA provides optimal sequence-specific binding and is preferred. The nucleic acid is often recombinant, meaning it comprises a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp.

The assay mixture also comprises a candidate pharmacological agent. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two Of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the IL-4 Stat peptide (or IL-4 Stat peptide containing polypeptide) selectively binds the cellular binding target, portion or analog. The mixture components can be added in any order that provides for the requisite bindings. Incubations may be performed at any temperature which facilitates optimal binding, typically between 4° and 40 ° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of selective binding between the IL-4 Stat peptide and one or more binding targets is detected by any convenient way. Often, a separation step is used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microliter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. Frequently, one of the components comprises or is coupled to a label. A wide variety of labels may be employed—essentially any label-that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, native emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. Candidate agents shown to inhibit IL-4 peptide—target binding or transcription complex formation provide valuable reagents to the pharmaceutical industries for animal and human trials.

The methods are particularly suited to automated high throughput drug screening. In a preferred embodiment, the individual sample incubation volumes are less than about 500 ul, preferably less than about 250 ul, more preferably less than about 100 ul. Such small sample volumes minimize the use of often scarce candidate agent, expensive transcription complex components, and hazardous radioactive waste. Furthermore, the methods provide for automation, especially computerized automation. Accordingly, the method steps are preferably performed by a computer-controlled electromechanical robot. While individual steps may be separately automated, a preferred embodiment provides a single computer-controlled multifunction robot with a single arm axially rotating to and from a plurality of work stations performing the mixture forming, incubating and separating steps. The computer is loaded with software which provides the instructions which direct the arm and work station operations and provides input (e.g. keyboard and/or mouse) and display (e.g. monitor) means for operator interfacing.

In another embodiment, the methods involve combining the first IL-4 Stat peptide (or peptide-containing polypeptide), a labelled form of an IL-4 Stat peptide binding target (e.g. a different transcription factor peptide (or peptide containing polypeptide)), the candidate pharmacological agent, a receptor immobilized on a solid substrate and the nucleic acid conjugated to a ligand capable of specifically binding the receptor.

The labelled target comprises a label that provides for detection of the labelled target when complexed, directly or indirectly, to the nucleic acid conjugate. The nucleic acid conjugate comprises an IL-4 Stat binding sequence, as previously described, coupled to a ligand. The ligand of the nucleic acid conjugate is capable of specifically binding the immobilized receptor. The ligand-receptor binding is specific enough to provide a maximized and at least measurable signal to noise ratio (receptor mediated vs. non-specific retention of the label on the substrate). The nucleic acid conjugate is typically capable of binding the receptor with an affinity of at least about $10^5M^{-1}$, preferably at least about $10^6M^{-1}$, more preferably at least about $10^8M^{-1}$. In a preferred embodiment, a plurality of ligands are capable of binding each receptor. Exemplary ligand-receptor pairs include biotin and avidin, antigen and antibody, sugar and lectin, ion and chelator, etc.

As above, the mixture usually includes additional reagents to facilitate optimal receptor-ligand and protein-nucleic acid binding or to reduce non-specific or background protein-substrate, nucleic acid-substrate, protein-protein and protein-DNA interactions, etc. The mixture is incubated under conditions whereby the receptor is bound to the ligand and, but for the presence of the candidate pharmacological agent, the IL-4 Stat peptide is sequence-specifically bound to the nucleic acid conjugate and the labelled target is selectively bound to the IL-4 Stat peptide. Incubations are as previously described. After receptor-ligand and protein-nucleic acid binding have occurred, a fraction comprising labelled target which is not directly or sequence-specifically bound through the IL-4 Stat peptide is separated from the solid substrate. This step may be accomplished in a variety of ways as described above. After separating the unbound fraction from the solid substrate, the presence of bound nucleic acid-protein complex is detected via the labeled target.

As previously described, the methods are particularly suited to automated high throughput drug screening: In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microtiter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates. Of course, useful agents are identified with a range of other assays (e.g. gel shifts, etc.) employing IL-4 Stat-peptides.

IL-4 Stat peptides and nucleic acids provide a wide variety of uses in addition to the in vitro binding assays described above. For example, cell-based assays are provided which involve transfecting an IL-4 receptor peptide (or peptide containing polypeptide, e.g. full length receptor) expressing cell such as ThP1 with an IL-4 Stat inducible reporter such as luciferase. Agents which modulate IL-4 Stat mediated cell function are then detected through a change in the reporter. Another approach is a transient expression assay. In this method, cells are transfected with one or more constructs encoding in sum, a polypeptide comprising a portion of IL-4 Stat capable of selectively binding an natural IL-4 target and a reporter under the transcriptional control of a promoter comprising a functional IL-4 Stat binding site. The cell may advantageously also be contransfected with a construct encoding an IL-4 Stat activator, usually a tyrosine kinase, particularly a Jak kinase.

The subject peptides provide useful lead compounds for designing structural analogs for use in binding assays and therapy (below). Additionally, the subject nucleic acids find use as hybridization probes for identifying IL-4 Stat cDNA homologs with substantial sequence similarity. Given the subject probes, materials and methods for probing cDNA and genetic libraries and recovering homologs are known in the art. Preferred libraries are derived from human immune cells, tumor cells, and neural cells; more preferred are cDNA libraries from differentiated human lymphoid cells. These IL-4 Stat cDNA homologs in turn provide additional Stat peptides for use in binding assays and therapy as described herein.

The subject compositions also provide therapeutic applications. For example, IL-4 Stat peptides or IL-4 receptor peptides such as the inhibitory peptides $NH_2$-GPPGEAGYKAFSSLL(SEQ ID NO:10)-COOH and $NH_2$-ASSGEEGYKPFQDLI(SEQ ID NO:11)-COOH, and phosphotyrosine containing portions thereof, find use in treating disease associated with undesirable cell growth, differentiation, particularly immune cell differentiation, and cytokine, particularly interleukin, more particularly IL-4, responsiveness. For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 μg/kg of the recipient. For peptide agents, the concentration of will generally be in the range of about 100 to 500 μg/ml in the dose administered. Other additives may be included, such as stabilizers, bactericides, etc. These additives will be present in conventional amounts.

IL-4 Stat peptide-and IL-4 receptor-encoding nucleic acids find use in therapeutic gene therapy. For example, such nucleic acids are cloned into a virus and the virus used to transfect and confer cytokine responsiveness to tumor cells. For gene therapy involving the transfusion of IL-4 Stat transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

EXPERIMENTAL

Interleukin-4 (IL-4), like IFN-g, rapidly alters the pattern of gene expression in cells bearing its cognate receptor. B lymphocytes, when exposed to IL-4, activate the synthesis of sterile transcripts of the immunoglobulin locus and subsequently undergo class switching to the IgE heavy chain isotype (Coffman et al., 1993). IL-4 also activates genes encoding cell surface proteins including various immunoglobulin receptors and the MHC class II antigen (Noelle et al., 1984: Roehm et al., 1984; Defrance et al., 1987; Hudak et al., 1987; Conrad et al., 1987). Like with IFN-g, a latent DNA binding protein is rapidly phosphorylated on tyrosine and translocated to the nucleus in receptor-bearing cells treated with IL-4 (Kohler and Rieber, 1993; Kotanides and Reich, 1993; Schindler et al., 1994). We disclose here the purification the IL-4 induced DNA binding protein and the cloning of its encoding gene.

Purification of an IL-4 Induced DNA Binding Protein

Human monocytic Thp-1 cells were grown in suspension, exposed briefly to IL-4, harvested, disrupted and fractionated to separate nuclear and cytoplasmic proteins. Nuclear extracts prepared from IL-4 treated cells, but not control cells, were observed to contain a DNA binding activity capable of specific interaction with a double stranded, synthetic oligonucleotide corresponding to the IL-4 response element located upstream of the human FcgRI gene (Kotanides and Reich, 1993). This activity was purified by a combination of three chromatographic steps and found to be specified by a polypeptide that migrated with a molecular mass of roughly 100 Kd when sized by denaturing polyacrylamide gel electrophoresis. The 100 Kd polypeptide reacted with an anti-phosphotyrosine antibody, consistent with earlier studies that had implicated tyrosine phosphorylation as an essential step required for its activation (Kotanides and Reich, 1993; Kohler and Rieber, 1993; Schindler et al., 1994).

The purified, 100 Kd polypeptide was digested with lys-C and resulting peptides were fractionated by capillary HPLC. Amino acid sequences were obtained from six peptide fragments. Synthetic oligonucleotides designed from these sequences were used for PCR amplification of cDNA prepared using mRNA from Thp-1 cells. This led to the isolation of a PCR fragment encoding three of the sequenced peptides. cDNA clones were obtained and sequenced, allowing prediction of the open reading frame corresponding to the 100 Kd polypeptide. Starting with an initiator methionine codon located 182 base pairs downstream from 5' terminus of the longest cDNA clone, the sequence predicts an open reading frame 848 residues in length. All six of the peptide sequences generated by lys-C digestion of the purified 100Kd polypeptide were found in the conceptually translated open reading frame.

A search of the NCBI BLAST data base revealed substantive similarity between the primary amino acid sequence of the 100 Kd, IL-4 induced protein and that of mammary gland factor (MGF), a prolactin induced DNA binding protein belonging to the Stat family of transcription factors (Wakao et al., 1994). Albeit less striking, sequence similarity was also observed between the IL-4 induced protein and the remaining four members of the Stat family. Table II provides a comparison of the amino acid sequence of the IL-4 induced protein with the sequences of the other known members of the Stat family of transcription factors.

TABLE II

STAT alignment (7/5) Formatted Alignment

| | | |
|---|---|---|
| IL-4 STAT (SEQ ID NO:02) (7.5) | MSLWGLVSKM PPE---KVQR LYVD--PPQH LRQLLGDWLR AQPWGFLVGS CAFCCNKASA LLSDTVQELQ ASVGEQ-GEG STILQ----- | 79 |
| STAT 5 (SEQ ID NO:16) | MAGWIQAQQL QGDALRQMQV LYGQ-HPPIS VREYIAQWIE SQPWGAIDLD NPQDRAQELQ LLEGLVQELQ KKAEHQVGED GFLLKIKLGH | 89 |
| STAT 1 (SEQ ID NO:12) | MSQWYELCQL DSKFLEQVHQ LYDDS-PPME IRQYLAQWLE KQDWEHAA-- NDV--SFATI RFHDLLSQLH DQYSRFSLE- NNPLLQHNIR | 84 |
| STAT 3 (SEQ ID NO:14) | MAQWNQLQQL DTRYLEQLHQ LYSDS-PPMH LRQFLAPWIE SQDWAYAA-- SKE--SHATL VFHNLLGEID QQYSRFLQE- SNVLYQHNLR | 84 |
| STAT 2 (SEQ ID NO:13) | MAQWEMLQNL DSPFQDQLHQ LYSHSLIPVD IRQYLAVWIE CQNWQEAALG SDD--SKATM LFFHFKDQLN YECGRCSQDP ESLLLQHNLR | 88 |
| STAT 4 (SEQ ID NO:15) | MSQWNQVQQL EIKFLEQVDQ FYDDN-PPMB IRHLLAQWIE IQDWEVAS-- NNE--TMATI LLQNLLIQLD EQLGRVSKE- KNLLLIHNLK | 84 |
| Consensus (SEQ ID NO:17) | M QW..QQL. ...L.Q..Q LY.Q.-PP.R .R..LA.WIE .Q.W..A... ...--..AT. L...L...L. ....R..... ...L..HN.. | 90 |
| IL-4 STAT (7.5) | --HIST---- -------LES L----YQRDP LKLVAT---- FRQIL---QG EKK-AVMEQF RHLPMPPHWK QEELK----- ---FKTGLR- | 135 |
| STAT 5 | YVHVSSRTRT TAAPWSWLRC LRHILYNEQR LVREATNGNS SAGILVDAMS QKHLQINQTF EELRLVTQDT ENELKKLQQT QEYFIIQYQE | 179 |
| STAT 1 | KSKRNLQDNF QEDPIQMSMI IYSCLKKERK ILENAQ---- -RFNQ--AQS GNIQSTVMLD KQKELDSKVR NVKDK-VMCI EHEIKSLEDL | 166 |
| STAT 3 | RIKQFLQSRY LEKPMEIARI VARCLWEESR LLQTAA---- -TAAQQGGQA NHPTAAVVTE KQQMLEQHLQ DVRKR-VQDL EQKMKVVENL | 168 |
| STAT 2 | KFCRDIQ-PF SQDPTQLAEM IFNLLLEEKR ILIQAQ---- -RAQL--EQG EPVLETPVES QQHEIESRIL DLRAM-MEKL VKSISQLKDQ | 169 |
| STAT 4 | RIRKVLQGKF HGNPMHVAVV LSNCLREERR ILAAAN---- -MPIQ-GPLE KSLQSSSVSE RQRNVEHKVS AIKNS-VQMT EQDTKYLEDL | 167 |
| Consensus | ......Q... ...P...... L...L.EE.R .L..A----- -....-..Q. .......... .Q........ .....-.... ....K..... | 180 |
| IL-4 STAT (7.5) | --RLQHRVGE IHLL--REAL QKGA--WAGQ VSLHSLLETP ANGTGP-SEA LAMLLQETTG ELEAAKALVL KRIQI-WKRQ QQLAGNGAPF | 217 |
| STAT 5 | SLRIQAQFAQ LAQLNPQERL SRETALQQKQ VSLEAWEQRE AQTLQQYEVE LAEKHQKTLQ LLRKQQTIIL DDELIQWKRR HLWRGMENP- | 268 |
| STAT 1 | QDEYDFKCKT LQNRE--HET NGVA--KSDQ KQEQLLLKKM YLMLDNKRKS VVHKIIELLN VTELTQNALI NDELVEWKRR QQSACIGGPP | 252 |
| STAT 3 | QDDFDFNYKT LKSQGDMQDL NGNN--QSVT RQKMQQLEQM LTALDQMRRS IVSELAGLLS AMEYVQKTLT DEELADWKRR QQIACIGGPP | 256 |
| STAT 2 | QDVFCFRYK- IQAKG---KT PSLD--PHQT KEQK-ILQET LNELDKRRKE VLDASKALLG RLT-TLIELL LPKLEEQKAQ QQKACIRAPI | 251 |
| STAT 4 | QDEFDYRYKT IQTMD---QG DKNS--ILVN QEVLTLLQEM LCSLDFKRKQ ALSKMTQIVN ETDLLMNSML LEELQDWKKR QQIACIGGPL | 252 |
| Consensus | QD......K. ....-..... ...--..... .......... ...LD..R.E .........L. .........L ..EL..WKRR QQ.ACIG.P. | 270 |

TABLE II-continued

| | | |
|---|---|---|
| IL-4 STAT (7.5) | EESLAPLQER CESLVDIY-- ----SQLQQE VGAAG---GE L--------E PKTR--ASLT GRLDEVLRTL VTSCFLVEKQ P--PQVLKTQ | 286 |
| STAT 5 | PRSLQVLQSW CEKLAEII-- ----WQNRQQ IRRAEHLCQQ LPIP-----G PVEEMLAEVN ATITDIISAL VTSTFIIEKQ P--PQVLKTQ | 345 |
| STAT 1 | NACLDQLQQ- ---------- ---------- VRQQLKKLEE LEQKYTYEHD PITKNKQVLW DRTFSLFQQL IQSSEVVERQ PCMPTHPQRP | 321 |
| STAT 3 | NICLQRLENWI TSLAESQLQ TRQQIKKLEE LHQKV----- -----SYKGD PIVQHRPMLE ERIVELFRNL MKSAFVVERQ PCMPMHPDRP | 336 |
| STAT 2 | DHGLEQLETW FTAGA----- -----KLLFH LRQLLKELKG LSCLVSYQDD PLTKGVDLRN AQVTELLQFL LHRAFVVEIQ PCMPQTPHRP | 331 |
| STAT 4 | HNGLDQLQNC FTLLAESLFQ LRQQLEKLQE QSTKM----- -----TYEGD PIPAQRAHLL ERATFLIYNL FKNSFVVERQ PCMPTHPQRP | 332 |
| Consensus | ...LO.LQ.. ...LA...-- ----...... .......... L...-.Y..D P.......L. .R...L...L ..S.FVVE.Q PCMP..P.RP | 360 |

| | | |
|---|---|---|
| IL-4 STAT (7.5) | TKFQAGVRFL LGLRFL-GAP AKPPLVRADM VTEKQARELS VPQGPGAGAE STGEIINNTV PLENSIPGNC CSALFKNLLL KKIKRCERKG | 375 |
| STAT 5 | TKFAATVRLL VGGKL--NVH MNPPQVKATI ISBQQAKSL- -LKNENTRNE CSGEILNNCC VMEYHQRTGT LSAHFRNMSL KRIKRADRRG | 431 |
| STAT 1 | LVLKTGVQFT VKLRLLVKLQ ELNYNLKVKV LFDKDVNERN TVKGFRKFNI LGTHTKVMNM EESTNGSLAA EFRHLQLKEQ K-NAGTRTN- | 409 |
| STAT 3 | LVIKTGVQFT TKVRLLVKFP ELNYQLKIKV CIDKDSGDVA ALRGSRKFNI LGTNTKVMNM EESNNGSLSA EFKHLTLREQ KCGNGGRANC | 426 |
| STAT 2 | LILKTGSKFT VRTRLLVRLQ EGNESLTVEV SIKRNPPQ-- -LQGFRKFNI LTSNQKTLTP EKGQSQGLIW DFGYLTLVEQ RSGGSGKGSN | 418 |
| STAT 4 | MVLKTLIQFT VKLRLLIKLP ELNYQVKVKA SIDKNVST-- -LSN-RRFVL CGTHVKAMSS EESSNGSLSV EFRHLQPKEM KCSTGSKGN- | 417 |
| Consensus | ...KTGV.FT V..RLL.... E.N...K... ..DK...... .L.G.R.FN. .....K.... E......L.. .F.HL...E. K......... | 450 |

| | | |
|---|---|---|
| IL-4 STAT (7.5) | TESVTEEKCA VLFSASFTLG PGKLPIQLQA LSLPIVVIVH GNQDNNAKAT IIQDNAF-SE MDRVP-FVVA ERVPWEKMCE TLNLKFMAEV | 463 |
| STAT 5 | AESVTEEKFT VLFESQFSVG SNELVFQVKT LSLPVVVIVH GSQDHNATAT VLWDNAF-AE PGRVP-FAVP DKVLWPQLCE ALNMKFKAEV | 519 |
| STAT 1 | EGPLIVTEEL HSLSFETQLC QPGLVIDLET TSLPVVVISN VSQLPSGWAS ILWYNMLVAE PRNLSRFLTP PCARWAQLSE VLSWQFSSVT | 499 |
| STAT 3 | DASLIVTEEL HLITFEREVY HQGLKIDLET JSLSVVVISN ICQMPNAWAS ILWYNMLTNN PKNVNFFTKP PIGTWDQVAE VLSWQFSSTT | 516 |
| STAT 2 | KGPLGVTEEL HIISFTVKYT YQGLKQELKT DILPVVIISN MNQLSIAWAS VLWFNLLSPN LQNQQFFSNP PKAPWSLLGP ALSWQFSSYV | 508 |
| STAT 4 | EGCHMVTEEL HSITFETQIC LYGLTINLET SSLPVVMISN VSQLPNAWAS IIWYNVSTND SQNLVFFNNP PSVTLGQLLE VMSWQFSSYV | 507 |
| Consensus | .....VTEEL H...F..... ..GL.I.L.T .SLPVVVISN ..Q..NAWAS ILW.N..... ...N..FF.. P.P...W.QL .E.LSWQFSS .V | 540 |

| | | |
|---|---|---|
| IL-4 STAT (7.5) | GTNRGLLPEH FLFLAQKLFN DNSLSMEAFQ HRSVSWSQFN KEILLGRGFT FWQWFDGVLD LTKRCLRSYW SDRLIIGFIS KQYVTSILLN | 553 |
| STAT 5 | QSNRGLTKEN LLFLAQKLFN NSSSHLEDYN GMSVSWSQFN KENLPGWNYT FWQWFDGVME VLKKHHKPHW NDGAILGFVN KQQAHDLLIN | 609 |
| STAT 1 | --KRGLNVDQ LNMLGEKLLG PNA----SPD G-LIPWTRFC KENINDKNFP FWLWIESILE LIKKHLLPLW NDGCIMGFIS KERERALLKD | 582 |
| STAT 3 | --KRGLSIEQ LTTLAEKLLG PGV----NYS GCQITWANFC KENMAGKGFS YWVWLDNIID LVKKYILALW NEGYIMGFIS KERERALLST | 600 |
| STAT 2 | --GRGLNSDQ LSMLRNKLFG QNC----RTE DPLLSWADFT KRESPPGKLP FWIWLDKILE LVHDHLKDLW NDGRIMGFVS RSQERRILKK | 592 |
| STAT 4 | --GRGLNSEQ LNMLAEKLTV QS-----NYN DGHLTWAKFC KEHLPGKTFT FWIWLEAILD LIKKHILPLW IDGYIMGPVS KEKERLLLKD | 590 |
| Consensus | --.RGL..EQ L..LA.KL.. ..------.. .....W..F. KE...G..F. FW.W.D.TL. L.KKH...LW NDG.IMGP.S K..ER.LL.. | 630 |

TABLE II-continued

| | | |
|---|---|---|
| IL-4 STAT (7.5) | EPDGTFLLRF SCSEIGG-FT IAHVIR-GQD GSPQIENIQP FSAKDLSIRS LGDRIRDLAQ LK-NLYPKKP KDEAFRSHYK PEQMGKDGRG | 640 |
| STAT 5 | KPDGTFLLRP SCSEIGG-FT IAWKFD-SPD --RNLWNLKP FTTREGSIRS LADRLGDLNY LI-YVFPDRP KDEVFSKYYT P-VLAKAVDG | 693 |
| STAT 1 | QQPGTFLLRF SESSREGAYT FTWVERSQNG GEPDFHAVEP YTKKELSAVT FPDIIRNYKV MAAENIPENP LKYLYPNIDK DHAFGKYY-- | 670 |
| STAT 3 | KPPGTFLLRF SESSKEGGVT FTWVEK-DIS GKTQIQSVEP YTKQQLNNMS FAEIIMGYKI MDATNILLSP LVYLTPDIPK EEAFGKY--- | 686 |
| STAT 2 | TMSGTFLLRF SESSEGG-YT CSWVEH-QDD DKVLIYSVQP YTKEVLQSLP LTEIIRHYQL LTEENIPENP LRFLYPRIPR DEADGCYYQE | 680 |
| STAT 4 | KMPGTFLLRF SESHLGG-FT FTWVDQSENG E-VRFHSVEP YNKGPLSALA FADILRDYKV IMAENIPENP LKYLYPDIPK DKAFGKHY-- | 676 |
| Consensus | ...GTFLLRF SES..GG-FT ..WV..-... .......V.P YTK..LS... ..DIIIR.Y. .....NIP..P L..LYP.I.K ..AFGK.... | 720 |
| IL-4 STAT (7.5) | YVPATIKMTV ERDQPLPTPE LQMPTMVPSY DLGMAPDSSM SMQLGPDMVP QVYPPHSHSI PPYQGLSPEE SVNVLSAFQE PHLQMPPSLG | 730 |
| STAT 5 | YVKPQIK--- ---------- ----QVVPEF -VSASADSA- ----GS---- ---------- ---------- ---------- RHLH------ | 720 |
| STAT 1 | -----SRPK- ---------- ----EAPEP- -MELDGPKG- ---------- ---------- ---------- ---------T GYIKTEL--- | 695 |
| STAT 3 | -----CRP-- ---------- ----ESQEH- -PEADPGSA- ---------- ---------- ---------- ---------A PYLKTKF--- | 710 |
| STAT 2 | KVNLQERRKY LKHRLIVVSN RQVDELQQP- -LELKPEPE- ---------- ---------L ESLELELGLV PEPELSLDLE PLLKAGLGLG | 748 |
| STAT 4 | ----SSQPC- ---------- ----EVSRP- -TE-RGDKG- ---------- ---------- ---------- ---------- -YVPSVF--- | 699 |
| Consensus | .........- ---------- ----E....- -.E......- ---------- ---------- ---------- ---------. ..L....--- | 810 |
| IL-4 STAT (7.5) | QMSLPFDQPH PQGLLPCQPQ EHAVSSPDPL LCSDVTMVED SCLSQPVTAF PQGTWIGEDI FPPLLPPTEQ DLTKLLLEGQ GESGGGSLGA | 820 |
| STAT 5 | ---------- ---------- -----GPGSL ---------- ---------- ---------- -PSRVPP--- ---------- -----ASL-- | 734 |
| STAT 1 | ---------- --------IS -VSEVHPSRL Q------TTD NLLP-----M SPEEFD---- --EVSRIVGS VE-------- ----FDSM-- | 735 |
| STAT 3 | ---------- --------IC -VTPTTCS-- N------TID --LP-----M SPRALD---- --SLMQFGNN GE---GAEPS AGGQFESLTF | 757 |
| STAT 2 | PELESVLEST LEPVIEPTLC MVSQTVPEPD QGPVSQPVPE PDLPCDLRHL NTEPMEIFRN CVKIEEIMPN GDPLLAGQNT VDEVYVSRPS | 838 |
| STAT 4 | ---------- --------IP -ISTIRSDST E----PQSPS DLLP-----M SPSATA---- --VLRENLSP TT-------- ----IETA-- | 741 |
| Consensus | ---------- --------.. -.....P... .----..... ..LP-----. .....---- -......... ..---..... ......S... | 900 |
| IL-4 STAT (7.5) | QPLLQPSHYG QSGISMSHMD LRANPSWX | 848 |
| STAT 5 | ---------- ---------- -------- | 734 |
| STAT 1 | --M------- -NTVX----- -------- | 740 |
| STAT 3 | D-MELTSECA TSPMX----- -------- | 771 |
| STAT 2 | H-FYTDGPLM PSDFX----- -------- | 852 |
| STAT 4 | --MN-----S PYSAE----- -------- | 749 |
| Consensus | .-........ .....----- -------- | 928 |

In all cases, the most significant segments of sequence similarity corresponded to three regions, one consisting of roughly 50 amino acids located at the amino termini of all six proteins and two more centrally located regions that have been predicted to specify SH2 and SH3 domains. Given the high degree of relatedness of the IL-4 induced protein to Stat proteins, coupled with its rapid, phosphotyrosine associated conversion from latent to active state, we have designated this protein IL-4 Stat.

Northern blotting assays confirmed the presence of an IL-4 Stat mRNA approximately 4 kilobases in length. This mRNA species was observed in a wide variety of human tissues, with highest levels occurring in placenta, lung, liver, kidney, thymus, prostate, ovary and peripheral blood lymphocytes. Northern blotting also revealed a slightly smaller mRNA that was observed most abundantly in kidney. Three larger mRNA species roughly 4.8, 5.5 and 6 kilobases in length were also observed. The 4.8 and 6 kilobase species were observed most abundantly in spleen and thymus, whereas the 5.5 kilobase species was only observed in peripheral blood lymphocytes.

Inhibition of IL-4 Stat DNA Binding Activity by Receptor Peptides

The IL-4 receptor complex is composed of two distinct polypeptides, a 139 Kd ligand binding subunit (IL-4R) and a smaller polypeptide (IL-2Rg) also utilized for IL-2 and IL-13 signaling (Ohm and Paul, 1987; Mosley et al., 1989; Noguchi et al., 1993; Russell et al., 1993). Inspection of the primary amino acid sequences of the intracellular domains of the two receptor subunits has not revealed obvious motifs capable of mediating signal transduction. IL-4 treatment of cultured cells does, however, bring about rapid tyrosine phosphorylation of the intracellular domain of the IL-4R subunit (Wang et al., 1992; Izuhara and Harada, 1993). Indeed, phosphorylation of tyrosine residue 472 (Y472) of the IL-4R has recently been implicated in signaling through a large cytoplasmic protein variously termed insulin receptor substrate-1 (IRS-1) or 4PS (Keegan et al., 1994). Having noted that the primary amino acid sequence of IL-4 Stat may specify an SH2 domain, we considered whether this domain might facilitate direct interaction with the intracellular domain of the IL-4 receptor at some point in the IL-4 Stat activation cycle.

In order to investigate possible coupling between the IL-4 receptor and the transcription factor it appears to activate, we examined the inhibitory effects of five phosphotyrosine peptides derived from the intracellular domain of the human IL-4R receptor on DNA binding by activated IL-4 Stat. As a control we also tested the inhibitory activity of the phosphotyrosine peptide of the IFN-g receptor that had previously been shown to potently block p91 activation (Greenlund et al., 1994). Each peptide contained a centrally located phosphotyrosine flanked on NH2 and COOH sides by seven amino acids specified by the native sequence of the human IL-4R subunit (Mosley et al., 1989; Takeshita et al., 1992). Samples of nuclear extract prepared from IL-4 induced Thp-1 cells were incubated with individual phosphopeptides then tested by the gel mobility shift assay for the retention of active IL-4 Stat. Two of the five phosphopeptides derived from the intracellular domain of the IL-4R subunit inhibited the DNA binding activity of IL-4 Stat at concentrations ranging from 100 to 300 uM. The IFN-g derived phosphopeptide did not affect DNA binding activity. Moreover, the activities of both of the inhibitory, IL-4R derived peptides were critically dependent upon tyrosine phosphorylation. Non-phosphorylated peptides showed no inhibitory activity.

Surprisingly, the two inhibitory peptides derived from the IL-4R are related in primary amino acid sequence, (NH2-GPPGEAGYKAFSSLL(SEQ ID NO:10)-COOH and NH2-ASSGEEGYKPFQDLI(SEQ ID NO:11)-COOH). It is notable that, relative to the centrally located phosphotyrosine, the two peptides are identical at the +1 and +3 positions. Detailed studies of SH2:phosphytyrosine peptide interaction have suggested that the +1 and +3 positions may be important for specifying selectivity of phosphotyrosine peptide:SH2 interaction (Songyang et at., 1993; Marengere et al., 1994).

To test whether the IL-4 receptor derived phosphopeptides might interact directly with IL-4 Stat, we examined the effects of five synthetic peptides on the DNA binding activity of the purified transcription factor. IL-4 Stat purified from IL-4 induced Thp-1 cells was incubated with the two IL-4 receptor-derived phosphopeptides that had shown inhibitory activity when tested in crude nuclear extracts. Corresponding non-phosphorylated versions of each peptide were also assayed, as was the tyrosine phosphorylated peptide derived from the IFN-g receptor that had been shown to inhibit activation of p91 in previous studies (Greenlund et al., 1994). We again observed phosphotyrosine dependent inhibition by the two IL-4R derived peptides and no discernible inhibitory effect by the IFN-g phosphopeptide.

As judged by Coomassie staining, the IL-4 Stat used in the present study was pure. Given that the two receptor-derived, inhibitory peptides were capable of complete elimination of IL-4 Stat DNA binding activity, any indirect made of inhibition must invoke a catalytic mechanism. One such mechanism might entail dephosphorylation of IL-4 Stat, a possibility eliminated by immunoblot assays using antibodies specific to phosphotyrosine. Following complete inhibition of IL-4 Stat DNA binding activity by incubation with 300 uM of the inhibitory phosphopeptides, protein was analyzed by We,stem blotting using anti-phosphotyrosine antibodies. As judged by this assay, IL-4 Stat does not lose phosphotyrosine as a result of exposure to the receptor-derived, inhibitory peptides.

Receptor-derived phosphotyrosine peptides inhibit IL-4 Stat dimerization

How might the inhibitory peptides derived from the IL-4 receptor block the DNA binding activity of purified IL-4 Stat? The inhibitory activity of both receptor-derived peptides required phosphorylation on tyrosine. Moreover, the inhibitory peptides were related in primary amino acid sequence on the immediate carboxyl terminal side of the phosphorylated tyrosine, a region which may play a role in specifying interaction between phosphotyrosine peptides and SH2 domains (Songyang et at., 1993). We imagined that these inhibitory peptides might bind to the SH2 domain of IL-4 Stat, thereby disrupting the reciprocal SH2:phosphotyrosine interactions that otherwise facilitate dimer adherence.

In order to test whether IL-4 Stat indeed exists in a dimeric state, purified protein was exposed independently to two chemical crosslinkers, glutaraldehyde and DSG. Both reagents caused time dependent crosslinking of IL-4 Stat to covalently linked dimers. Even when exposed for a length of time sufficient to quantitatively crosslink all IL-4 Stat to covalently linked dimers, no evidence of higher order (trimeric or tetrameric) oligomerization was observed. The limit nature of this cross linking, coupled with the fact that it was observed at a very low protein concentration, provides firm evidence that functional IL-4 Stat exists in a dimeric state. This interpretation is consistent with studies of other Stat proteins (Shuai et al., 1994). It likewise fits with the dyad symmetric nature of the seven IL-4 Stat binding sites identified thus far (Kotanides and Reich, 1993).

Chemical crosslinking provided a means of testing whether the monomer:dimer equilibrium of IL-4 Stat might be influenced by the IL-4 receptor-derived peptides that were observed to inhibit DNA binding. Purified IL-4 Stat was exposed to the same five peptides that were tested in the DNA binding inhibition assay. Following a brief incubation interval the samples were exposed to DSG under conditions sufficient to quantitatively crosslink IL-4 Stat. The two IL-4 receptor derived peptides, if phosphorylated on tyrosine, impeded formation of covalently linked IL-4 Stat in a concentration dependent manner. No effect was observed when non-phosphorylated variants of the same two peptides were tested. Likewise, the phosphopeptide derived from the IFN-g receptor did not impede DSG-mediated cross linking. The concentration at which receptor-derived phosphopeptides inhibit DNA binding corresponds closely with that required to impede crosslinking of IL-4 Stat dimers. We therefore conclude that incubation of IL-4 Stat with tyrosine phosphorylated peptides derived from the intracellular domain if its cognate receptor influences monomer:dimer equilibrium, and that the disassociation of IL-4 Stat dimers represents the mechanism by which receptor-derived phosphopeptides inhibit DNA binding.

From the foregoing observations, we conclude that IL-4 Stat activation entails transient coupling with either or both of two specific tyrosine residues, Y578 and Y606, located in the intracellular domain of the IL-4 receptor. Given that the inhibitory activities of synthetic peptides corresponding to these regions of the IL-4 receptor require tyrosine phosphorylation, transient receptor coupling of IL-4 Stat is likewise be dependent upon tyrosine phosphorylation. These findings are at odds with functional studies of the IL-4R subunit which have shown that mutated variants of the receptor lacking all tyrosines native to the intracellular domain can mediate the growth stimulatory effects of IL-4 as tested in the murine pro-B cell line, Ba/F3 (Seldin and Leder, 1994). Surprisingly, the readout of the Ba/F3 assay, mitotic proliferation, must also be independent of IL-4 mediated activation of IRS-1. Tyrosine 472 of the IL-4R subunit has been firmly implicated in the IL-4 induced phosphorylation of IRS-1 and proliferative response of human macrophage 32D cells (Keegan et al., 1994).

A second conclusion from the studies reported herein derives from the ability of IL-4 receptor-derived phosphopeptides to selectively inhibited DSG-mediated crosslinking of IL-4 Stat. Such inhibition was observed at concentrations similar to those required to inhibit DNA binding activity. These results indicate that the inhibitory peptides dissociate IL-4 Stat dimers, thereby causing an inhibition of DNA binding activity. We further conclude that IL-4 Stat utilizes the same polypeptide domain to mediate transient receptor interaction and dimerization.

The following examples are offered by way of illustration and not by way of limitation.

EXAMPLES

1. Protocol for IL-4 Stat—IL-4 Stat dependent transcription factor binding assay.

A. Reagents

IL-4 Stat: 20 μg/ml activated, truncated (SH2 domain) IL-4 Stat in PBS.

Blocking buffers: 5% BSA, 0.5% Tween 20 in PBS; 1 hr, RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P IL-4 Stat 10× stock: $10^{-8}$–$10^{-6}$M "cold" IL-4 Stat homolog supplemented with 200,000–250,000 cpm of labeled IL-4 Stat homolog (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

B. Preparation of assay plates

Coat with 120 μl of stock IL-4 Stat per well overnight at 4° C.

Wash 2× with 200 μl PBS.

Block with 150 μl of blocking buffer.

Wash 2× with 200 μl PBS.

C. Assay

Add 80μl assay buffer/well.

Add 10 μl compound or extract.

Add 10 μl $^{33}$P-IL-4 Stat (20,000–25,000 cpm/0.3 pmoles/well=$3\times10^{-9}$M final concentration).

Shake at 25C for 15 min.

Incubate additional 45 min. at 25C

Stop the reaction by washing 4× with 200 μl PBS.

Add 150 μl scintillation cocktail.

Count in Topcount.

D. Controls for all assays (located on each plate)

a. Non-specific binding (no IL-4 Stat added)

b. cold IL-4 Stat at 80% inhibition.

2. Protocol for IL-4 Stat—IL-4 Receptor-peptide binding assay.

A. Reagents

Neutralite Avidin: 20 μg/ml in PBS.

Blocking buffer: 5% BSA, 0.5% Tween 20 in PBS; 1 hr, RT.

Assay buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P IL-4 Stat 10× stock: $10^{-8}$–$10^{-6}$M "cold" inactive (not tyrphosporylated) and truncated (SH2 domain) IL-4 Stat supplemented with 200,000–250,000 cpm of labeled, inactive and truncated IL-4 Stat (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

IL-4receptor-peptides: $^{-}10^{-8}$–$10^{-5}$M of each IL-4 receptor biotinylated peptides: $NH_2$-GPPGEAGYKAFSSLL (SEQ ID NO:10)-COOH AND $NH_2$-ASSGEEGYKPFQDLI(SEQ ID NO:11)-COOH in PBS.

B. Preparation of assay plates

Coat with 120 μl of stock N-Avidin per well overnight at 4° C.

Wash 2× with 200 μl PBS.

Block with 150 μl of blocking buffer.

Wash 2× with 200 μl PBS.

C. Assay

Add 40 μl assay buffer/well.

Add 10 μl compound or extract.

Add 10 μl $^{33}$P-IL-4 Stat (20,000–25,000 cpm/0.1–10 pmoles/well=$10^{-9}$–$10^{-7}$M final concentration).

Shake at 25C for 15 min.

Incubate additional 45 min. at 25C.

Add 40 μl IL-4 Stat receptor peptide mixture (0.1–10 pmoles/40 ul in assay buffer)

Incubate 1 hr at RT.

Stop the reaction by washing 4× with 200 μl PBS.

Add 150 μl scintillation cocktail.

Count in Topcount.

D. Controls for all assays (located on each plate)

a. Non-specific binding (no receptor peptide added)

b. Soluble (non-biotinylated receptor peptide) at 80% inhibition.

3. Protocol for IL-4 Stat dependent transcription factor—DNA binding assay.

A. Reagents

Neutralite Avidin: 20 μg/ml in PBS.

Blocking buffer: 5% BSA, 0.5% Tween 20 in PBS; 1 hr, RT.

Assay Buffer: 100 mM KCl, 20 mM HEPES pH 7.6, 0.25 mM EDTA, 1% glycerol, 0.5% NP40, 50 mM BME, 1 mg/ml BSA, cocktail of protease inhibitors.

$^{33}$P IL-4 Stat 10× stock: $10^{-6}$–$10^{-8}$M "cold" IL-4 Stat (see above) supplemented with 200,000–250;000 cpm of labeled IL-4 Stat (Beckman counter). Place in the 4° C. microfridge during screening.

Protease inhibitor cocktail (1000×): 10 mg Trypsin Inhibitor (BMB #109894), 10 mg Aprotinin BMB #236624), 25 mg Benzamidine (Sigma #B-6056), 25 mg Leupeptin (BMB #1017128), 10 mg APMSF (BMB #917575), and 2 mM $NaVo_3$ (Sigma #S-6508) in 10 ml of PBS.

Oligonucleotide stock: (specific biotinylated). Biotinylated oligo at 17 pmole/μl IL-4 Stat binding site: (BIOTIN)-GTATTTCCCAGAAAAGGAAC(SEQ ID NO:13)

B. Preparation of assay plates

Coat with 120 μl of stock N-Avidin per well overnight at 4° C.

Wash 2× with 200 μl PBS.

Block with 150 μl of blocking buffer.

Wash 2× with 200 μl PBS.

C. Assay

Add 40 μl assay buffer/well.

Add 10 μl compound or extract.

Add 10 μl $^{33}$P-IL-4 Stat (20,000–25,000 cpm/0.1–10 pmoles/well=$10^{-9}$–$10^{-7}$M final concentration).

Shake at 25C for 15 min.

Incubate additional 45 min. at 25C.

Add 40 μl oligo mixture (1.0 pmoles/40 ul in assay buffer with 1 ng of ss-DNA)

Incubate 1 hr at RT.

Stop the reaction by washing 4× with 200 μl PBS.

Add 150 μl scintillation cocktail.

Count in Topcount.

D. Controls for all assays (located on each plate)

a. Non-specific binding (no oligo added)

b. Specific soluble oligo at 80% inhibition.

All publications and patent applications cited in this specification as herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the an in light of the teachings of this invention that certain changes and modifications may be made thereto without departing from the spirit or scope of the appended claims.

What is claimed is:

1. An isolated nucleic acid encoding an interleukin-4 signal transducer and activator of transcription (IL-4 STAT) protein wherein said protein:

(a) selectively binds a transcription factor binding site having a sequence selected from the group consisting of SEQ ID NO: 03, SEQ ID NO: 04, SEQ ID NO: 05, SEQ ID NO: 06, SEQ ID NO: 07, SEQ ID NO: 08 or SEQ ID NO: 09; and (b) selectively binds an IL-4 receptor peptide having a sequence defined by SEQ ID NO: 10 or SEQ ID NO: 11; and (c) is encoded by a DNA which hybridizes with SEQ ID NO:01 under high stringency conditions.

2. An isolated nucleic acid encoding an interleukin-4 signal transducer and activator of transcription (IL-4 STAT) protein, wherein said protein comprises at least one of the amino acid sequences selected from the group consisting of SEQ ID NO: 02, residues 1 to 40 and SEQ ID NO:02, residues 401 to 650.

3. An isolated nucleic acid encoding an interleukin-4 signal transducer and activator of transcription (IL-4 STAT) protein, wherein said protein comprises the amino acid sequence of SEQ ID NO:2.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 3046 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 166..2706

( x i ) SEQUENCE DESCRIPTION: SEQ ID NO:1:

```
ATCTTATTTT TCTTTTTGGT GGTGGTGGTG GAAGGGGGGA GGTGCTAGCA GGGCCAGCCT      60

TGAACTCGCT GGACAGAGCT ACAGACCTAT GGGGCCTGGA AGTGCCCGCT GAGAAAGGGA     120

GAAGACAGCA GAGGGGTTGC CGAGGCAACC TCCAAGTCCC AGATC ATG TCT CTG         174
                                                  Met Ser Leu
                                                    1

TGG GGT CTG GTC TCC AAG ATG CCC CCA GAA AAA GTG CAG CGG CTC TAT       222
```

-continued

```
Trp Gly Leu Val Ser Lys Met Pro Pro Glu Lys Val Gln Arg Leu Tyr
      5                  10                  15

GTC GAC TTT CCC CAA CAC CTG CGG CAT CTT CTG GGT GAC TGG CTG GAG      270
Val Asp Phe Pro Gln His Leu Arg His Leu Leu Gly Asp Trp Leu Glu
 20                  25                  30                  35

AGC CAG CCC TGG GAG TTC CTG GTC GGC TCC GAC GCC TTC TGC TGC AAC      318
Ser Gln Pro Trp Glu Phe Leu Val Gly Ser Asp Ala Phe Cys Cys Asn
                 40                  45                  50

TTG GCT AGT GCC CTA CTT TCA GAC ACT GTC CAG CAC CTT CAG GCC TCG      366
Leu Ala Ser Ala Leu Leu Ser Asp Thr Val Gln His Leu Gln Ala Ser
             55                  60                  65

GTG GGA GAG CAG GGG GAG GGG AGC ACC ATC TTG CAA CAC ATC AGC ACC      414
Val Gly Glu Gln Gly Glu Gly Ser Thr Ile Leu Gln His Ile Ser Thr
         70                  75                  80

CTT GAG AGC ATA TAT CAG AGG GAC CCC CTG AAG CTG GTG GCC ACT TTC      462
Leu Glu Ser Ile Tyr Gln Arg Asp Pro Leu Lys Leu Val Ala Thr Phe
     85                  90                  95

AGA CAA ATA CTT CAA GGA GAG AAA AAA GCT GTT ATG GAA CAG TTC CGC      510
Arg Gln Ile Leu Gln Gly Glu Lys Lys Ala Val Met Glu Gln Phe Arg
100                 105                 110                 115

CAC TTG CCA ATG CCT TTC CAC TGG AAG CAG GAA GAA CTC AAG TTT AAG      558
His Leu Pro Met Pro Phe His Trp Lys Gln Glu Glu Leu Lys Phe Lys
                120                 125                 130

ACA GGC TTG CGG AGG CTG CAG CAC CGA GTA GGG GAG ATC CAC CTT CTC      606
Thr Gly Leu Arg Arg Leu Gln His Arg Val Gly Glu Ile His Leu Leu
            135                 140                 145

CGA GAA GCC CTG CAG AAG GGG GCT GAG GCT GGC CAA GTG TCT CTG CAC      654
Arg Glu Ala Leu Gln Lys Gly Ala Glu Ala Gly Gln Val Ser Leu His
        150                 155                 160

AGC TTG ATA GAA ACT CCT GCT AAT GGG ACT GGG CCA AGT GAG GCC CTG      702
Ser Leu Ile Glu Thr Pro Ala Asn Gly Thr Gly Pro Ser Glu Ala Leu
    165                 170                 175

GCC ATG CTA CTG CAG GAG ACC ACT GGA GAG CTA GAG GCA GCC AAA GCC      750
Ala Met Leu Leu Gln Glu Thr Thr Gly Glu Leu Glu Ala Ala Lys Ala
180                 185                 190                 195

CTA GTG CTG AAG AGG ATC CAG ATT TGG AAA CGG CAG CAG CAG CTG GCA      798
Leu Val Leu Lys Arg Ile Gln Ile Trp Lys Arg Gln Gln Gln Leu Ala
                200                 205                 210

GGG AAT GGC GCA CCG TTT GAG GAG AGC CTG GCC CCA CTC CAG GAG AGG      846
Gly Asn Gly Ala Pro Phe Glu Glu Ser Leu Ala Pro Leu Gln Glu Arg
            215                 220                 225

TGT GAA AGC CTG GTG GAC ATT TAT TCC CAG CTA CAG CAG GAG GTA GGG      894
Cys Glu Ser Leu Val Asp Ile Tyr Ser Gln Leu Gln Gln Glu Val Gly
        230                 235                 240

GCG GCT GGT GGG GAG CTT GAG CCC AAG ACC CGG GCA TCG CTG ACT GGC      942
Ala Ala Gly Gly Glu Leu Glu Pro Lys Thr Arg Ala Ser Leu Thr Gly
    245                 250                 255

CGG CTG GAT GAA GTC CTG AGA ACC CTC GTC ACC AGT TGC TTC CTG GTG      990
Arg Leu Asp Glu Val Leu Arg Thr Leu Val Thr Ser Cys Phe Leu Val
260                 265                 270                 275

GAG AAG CAG CCC CCC CAG GTA CTG AAG ACT CAG ACC AAG TTC CAG GCT     1038
Glu Lys Gln Pro Pro Gln Val Leu Lys Thr Gln Thr Lys Phe Gln Ala
                280                 285                 290

GGA GTT CGA TTC CTG TTG GGC TTG AGG TTC CTG GGG GCC CCA GCC AAG     1086
Gly Val Arg Phe Leu Leu Gly Leu Arg Phe Leu Gly Ala Pro Ala Lys
            295                 300                 305

CCT CCG CTG GTC AGG GCC GAC ATG GTG ACA GAG AAG CAG GCG CGG GAG     1134
Pro Pro Leu Val Arg Ala Asp Met Val Thr Glu Lys Gln Ala Arg Glu
        310                 315                 320

CTG AGT GTG CCT CAG GGT CCT GGG GCT GGA GCA GAA AGC ACT GGA GAA     1182
```

-continued

Leu Ser Val Pro Gln Gly Pro Gly Ala Gly Ala Glu Ser Thr Gly Glu
325 330 335

ATC ATC AAC AAC ACT GTG CCC TTG GAG AAC AGC ATT CCT GGG AAC TGC 1230
Ile Ile Asn Asn Thr Val Pro Leu Glu Asn Ser Ile Pro Gly Asn Cys
340 345 350 355

TGC TCT GCC CTG TTC AAG AAC CTG CTT CTC AAG AAG ATC AAG CGG TGT 1278
Cys Ser Ala Leu Phe Lys Asn Leu Leu Leu Lys Lys Ile Lys Arg Cys
360 365 370

GAG CGG AAG GGC ACT GAG TCT GTC ACA GAG GAG AAG TGC GCT GTG CTC 1326
Glu Arg Lys Gly Thr Glu Ser Val Thr Glu Glu Lys Cys Ala Val Leu
375 380 385

TTC TCT GCC AGC TTC ACA CTT GGC CCC GGC AAA CTC CCC ATC CAG CTC 1374
Phe Ser Ala Ser Phe Thr Leu Gly Pro Gly Lys Leu Pro Ile Gln Leu
390 395 400

CAG GCC CTG TCT CTG CCC CTG GTG GTC ATC GTC CAT GGC AAC CAA GAC 1422
Gln Ala Leu Ser Leu Pro Leu Val Val Ile Val His Gly Asn Gln Asp
405 410 415

AAC AAT GCC AAA GCC ACT ATC CTG TGG GAC AAT GCC TTC TCT GAG ATG 1470
Asn Asn Ala Lys Ala Thr Ile Leu Trp Asp Asn Ala Phe Ser Glu Met
420 425 430 435

GAC CGC GTG CCC TTT GTG GTG GCT GAG CGG GTG CCC TGG GAG AAG ATG 1518
Asp Arg Val Pro Phe Val Val Ala Glu Arg Val Pro Trp Glu Lys Met
440 445 450

TGT GAA ACT CTG AAC CTG AAG TTC ATG GCT GAG GTG GGG ACC AAC CGG 1566
Cys Glu Thr Leu Asn Leu Lys Phe Met Ala Glu Val Gly Thr Asn Arg
455 460 465

GGG CTG CTC CCA GAG CAC TTC CTC TTC CTG GCC CAG AAG ATC TTC AAT 1614
Gly Leu Leu Pro Glu His Phe Leu Phe Leu Ala Gln Lys Ile Phe Asn
470 475 480

GAC AAC AGC CTC AGT ATG GAG GCC TTC CAG CAC CGT TCT GTG TCC TGG 1662
Asp Asn Ser Leu Ser Met Glu Ala Phe Gln His Arg Ser Val Ser Trp
485 490 495

TCG CAG TTC AAC AAG GAG ATC CTG CTG GGC CGT GGC TTC ACC TTT TGG 1710
Ser Gln Phe Asn Lys Glu Ile Leu Leu Gly Arg Gly Phe Thr Phe Trp
500 505 510 515

CAG TGG TTT GAT GGT GTC CTG GAC CTC ACC AAA CGC TGT CTC CGG AGC 1758
Gln Trp Phe Asp Gly Val Leu Asp Leu Thr Lys Arg Cys Leu Arg Ser
520 525 530

TAC TGG TCT GAC CGG CTG ATC ATT GGC TTC ATC AGC AAA CAG TAC GTT 1806
Tyr Trp Ser Asp Arg Leu Ile Ile Gly Phe Ile Ser Lys Gln Tyr Val
535 540 545

ACT AGC CTT CTT CTC AAT GAG CCC GAC GGA ACC TTT CTC CTC CGC TTC 1854
Thr Ser Leu Leu Leu Asn Glu Pro Asp Gly Thr Phe Leu Leu Arg Phe
550 555 560

AGC GAC TCA GAG ATT GGG GGC ATC ACC ATT GCC CAT GTC ATC CGG GGC 1902
Ser Asp Ser Glu Ile Gly Gly Ile Thr Ile Ala His Val Ile Arg Gly
565 570 575

CAG GAT GGC TCT CCA CAG ATA GAG AAC ATC CAG CCA TTC TCT GCC AAA 1950
Gln Asp Gly Ser Pro Gln Ile Glu Asn Ile Gln Pro Phe Ser Ala Lys
580 585 590 595

GAC CTG TCC ATT CGC TCA CTG GGG GAC CGA ATC CGG GAT CTT GCT CAG 1998
Asp Leu Ser Ile Arg Ser Leu Gly Asp Arg Ile Arg Asp Leu Ala Gln
600 605 610

CTC AAA AAT CTC TAT CCC AAG AAG CCC AAG GAT GAG GCT TTC CGG AGC 2046
Leu Lys Asn Leu Tyr Pro Lys Lys Pro Lys Asp Glu Ala Phe Arg Ser
615 620 625

CAC TAC AAG CCT GAA CAG ATG GGT AAG GAT GGC AGG GGT TAT GTC CCA 2094
His Tyr Lys Pro Glu Gln Met Gly Lys Asp Gly Arg Gly Tyr Val Pro
630 635 640

GCT ACC ATC AAG ATG ACC GTG GAA AGG GAC CAA CCA CTT CCT ACC CCA 2142

-continued

Ala Thr Ile Lys Met Thr Val Glu Arg Asp Gln Pro Leu Pro Thr Pro
645 650 655

GAG CTC CAG ATG CCT ACC ATG GTG CCT TCT TAT GAC CTT GGA ATG GCC 2190
Glu Leu Gln Met Pro Thr Met Val Pro Ser Tyr Asp Leu Gly Met Ala
660 665 670 675

CCT GAT TCC TCC ATG AGC ATG CAG CTT GGC CCA GAT ATG GTG CCC CAG 2238
Pro Asp Ser Ser Met Ser Met Gln Leu Gly Pro Asp Met Val Pro Gln
680 685 690

GTG TAC CCA CCA CAC TCT CAC TCC ATC CCC CCG TAT CAA GGC CTC TCC 2286
Val Tyr Pro Pro His Ser His Ser Ile Pro Pro Tyr Gln Gly Leu Ser
695 700 705

CCA GAA GAA TCA GTC AAC GTG TTG TCA GCC TTC CAG GAG CCT CAC CTG 2334
Pro Glu Glu Ser Val Asn Val Leu Ser Ala Phe Gln Glu Pro His Leu
710 715 720

CAG ATG CCC CCC AGC CTG GGC CAG ATG AGC CTG CCC TTT GAC CAG CCT 2382
Gln Met Pro Pro Ser Leu Gly Gln Met Ser Leu Pro Phe Asp Gln Pro
725 730 735

CAC CCC CAG GGC CTG CTG CCG TGC CAG CCT CAG GAG CAT GCT GTG TCC 2430
His Pro Gln Gly Leu Leu Pro Cys Gln Pro Gln Glu His Ala Val Ser
740 745 750 755

AGC CCT GAC CCC CTG CTC TGC TCA GAT GTG ACC ATG GTG GAA GAC AGC 2478
Ser Pro Asp Pro Leu Leu Cys Ser Asp Val Thr Met Val Glu Asp Ser
760 765 770

TGC CTG AGC CAG CCA GTG ACA GCG TTT CCT CAG GGC ACT TGG ATT GGT 2526
Cys Leu Ser Gln Pro Val Thr Ala Phe Pro Gln Gly Thr Trp Ile Gly
775 780 785

GAA GAC ATA TTC CCT CCT CTG CTG CCT CCC ACT GAA CAG GAC CTC ACT 2574
Glu Asp Ile Phe Pro Pro Leu Leu Pro Pro Thr Glu Gln Asp Leu Thr
790 795 800

AAG CTT CTC CTG GAG GGG CAA GGG GAG TCG GGG GGA GGG TCC TTG GGG 2622
Lys Leu Leu Leu Glu Gly Gln Gly Glu Ser Gly Gly Gly Ser Leu Gly
805 810 815

GCA CAG CCC CTC CTG CAG CCC TCC CAC TAT GGG CAA TCT GGG ATC TCA 2670
Ala Gln Pro Leu Leu Gln Pro Ser His Tyr Gly Gln Ser Gly Ile Ser
820 825 830 835

ATG TCC CAC ATG GAC CTA AGG GCC AAC CCC AGT TGG TGATCCCAGC 2716
Met Ser His Met Asp Leu Arg Ala Asn Pro Ser Trp
840 845

TGGAGGGAGA ACCCAAAGAG ACAGCTCTTC TACTACCCCC ACAGACCTGC TCTGGACACT 2776

TGCTCATGCC CTGCCAAGCA GCAGATGGGG AGGGTGCCCT CCTATCCCCA CCTACTCCTG 2836

GGTCAGGAGG AAAAGACTAA CAGGAGAATG CACAGTGGGT GGAGCCAATC CACTCCTTCC 2896

TTTCTATCAT TCCCCTGCCC ACCTCCTTCC AGCACTGACT GGAAGGGAAG TTCAGGCTCT 2956

GAGACACGCC CCAACATGCC TGCACCTGCA GCGCGCACAC GCACGCACAC ACACATACAG 3016

AGCTCTCTGA GGGTGATGGG GCTGAGCAGG 3046

( 2 ) INFORMATION FOR SEQ ID NO:2:

( i ) SEQUENCE CHARACTERISTICS:
( A ) LENGTH: 847 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Ser Leu Trp Gly Leu Val Ser Lys Met Pro Pro Glu Lys Val Gln
1 5 10 15

Arg Leu Tyr Val Asp Phe Pro Gln His Leu Arg His Leu Leu Gly Asp
20 25 30

-continued

Trp Leu Glu Ser Gln Pro Trp Glu Phe Leu Val Gly Ser Asp Ala Phe
35 40 45

Cys Cys Asn Leu Ala Ser Ala Leu Leu Ser Asp Thr Val Gln His Leu
50 55 60

Gln Ala Ser Val Gly Glu Gln Gly Glu Gly Ser Thr Ile Leu Gln His
65 70 75 80

Ile Ser Thr Leu Glu Ser Ile Tyr Gln Arg Asp Pro Leu Lys Leu Val
85 90 95

Ala Thr Phe Arg Gln Ile Leu Gln Gly Glu Lys Lys Ala Val Met Glu
100 105 110

Gln Phe Arg His Leu Pro Met Pro Phe His Trp Lys Gln Glu Glu Leu
115 120 125

Lys Phe Lys Thr Gly Leu Arg Arg Leu Gln His Arg Val Gly Glu Ile
130 135 140

His Leu Leu Arg Glu Ala Leu Gln Lys Gly Ala Glu Ala Gly Gln Val
145 150 155 160

Ser Leu His Ser Leu Ile Glu Thr Pro Ala Asn Gly Thr Gly Pro Ser
165 170 175

Glu Ala Leu Ala Met Leu Leu Gln Glu Thr Thr Gly Glu Leu Glu Ala
180 185 190

Ala Lys Ala Leu Val Leu Lys Arg Ile Gln Ile Trp Lys Arg Gln Gln
195 200 205

Gln Leu Ala Gly Asn Gly Ala Pro Phe Glu Glu Ser Leu Ala Pro Leu
210 215 220

Gln Glu Arg Cys Glu Ser Leu Val Asp Ile Tyr Ser Gln Leu Gln Gln
225 230 235 240

Glu Val Gly Ala Ala Gly Gly Glu Leu Glu Pro Lys Thr Arg Ala Ser
245 250 255

Leu Thr Gly Arg Leu Asp Glu Val Leu Arg Thr Leu Val Thr Ser Cys
260 265 270

Phe Leu Val Glu Lys Gln Pro Pro Gln Val Leu Lys Thr Gln Thr Lys
275 280 285

Phe Gln Ala Gly Val Arg Phe Leu Leu Gly Leu Arg Phe Leu Gly Ala
290 295 300

Pro Ala Lys Pro Pro Leu Val Arg Ala Asp Met Val Thr Glu Lys Gln
305 310 315 320

Ala Arg Glu Leu Ser Val Pro Gln Gly Pro Gly Ala Gly Ala Glu Ser
325 330 335

Thr Gly Glu Ile Ile Asn Asn Thr Val Pro Leu Glu Asn Ser Ile Pro
340 345 350

Gly Asn Cys Cys Ser Ala Leu Phe Lys Asn Leu Leu Leu Lys Lys Ile
355 360 365

Lys Arg Cys Glu Arg Lys Gly Thr Glu Ser Val Thr Glu Glu Lys Cys
370 375 380

Ala Val Leu Phe Ser Ala Ser Phe Thr Leu Gly Pro Gly Lys Leu Pro
385 390 395 400

Ile Gln Leu Gln Ala Leu Ser Leu Pro Leu Val Val Ile Val His Gly
405 410 415

Asn Gln Asp Asn Asn Ala Lys Ala Thr Ile Leu Trp Asp Asn Ala Phe
420 425 430

Ser Glu Met Asp Arg Val Pro Phe Val Val Ala Glu Arg Val Pro Trp
435 440 445

Glu Lys Met Cys Glu Thr Leu Asn Leu Lys Phe Met Ala Glu Val Gly

-continued

| | | | | | | | | | | | | | | | |
|---|---|---|---|---|---|---|---|---|---|---|---|---|---|---|---|
| | 450 | | | | | 455 | | | | | 460 | | | | |
| Thr | Asn | Arg | Gly | Leu | Leu | Pro | Glu | His | Phe | Leu | Phe | Leu | Ala | Gln | Lys |
| 465 | | | | | 470 | | | | | 475 | | | | | 480 |
| Ile | Phe | Asn | Asp | Asn | Ser | Leu | Ser | Met | Glu | Ala | Phe | Gln | His | Arg | Ser |
| | | | | 485 | | | | | 490 | | | | | 495 | |
| Val | Ser | Trp | Ser | Gln | Phe | Asn | Lys | Glu | Ile | Leu | Leu | Gly | Arg | Gly | Phe |
| | | | 500 | | | | | 505 | | | | | 510 | | |
| Thr | Phe | Trp | Gln | Trp | Phe | Asp | Gly | Val | Leu | Asp | Leu | Thr | Lys | Arg | Cys |
| | | 515 | | | | | 520 | | | | | 525 | | | |
| Leu | Arg | Ser | Tyr | Trp | Ser | Asp | Arg | Leu | Ile | Ile | Gly | Phe | Ile | Ser | Lys |
| | 530 | | | | | 535 | | | | | 540 | | | | |
| Gln | Tyr | Val | Thr | Ser | Leu | Leu | Leu | Asn | Glu | Pro | Asp | Gly | Thr | Phe | Leu |
| 545 | | | | | 550 | | | | | 555 | | | | | 560 |
| Leu | Arg | Phe | Ser | Asp | Ser | Glu | Ile | Gly | Gly | Ile | Thr | Ile | Ala | His | Val |
| | | | | 565 | | | | | 570 | | | | | 575 | |
| Ile | Arg | Gly | Gln | Asp | Gly | Ser | Pro | Gln | Ile | Glu | Asn | Ile | Gln | Pro | Phe |
| | | | 580 | | | | | 585 | | | | | 590 | | |
| Ser | Ala | Lys | Asp | Leu | Ser | Ile | Arg | Ser | Leu | Gly | Asp | Arg | Ile | Arg | Asp |
| | | 595 | | | | | 600 | | | | | 605 | | | |
| Leu | Ala | Gln | Leu | Lys | Asn | Leu | Tyr | Pro | Lys | Lys | Pro | Lys | Asp | Glu | Ala |
| | 610 | | | | | 615 | | | | | 620 | | | | |
| Phe | Arg | Ser | His | Tyr | Lys | Pro | Glu | Gln | Met | Gly | Lys | Asp | Gly | Arg | Gly |
| 625 | | | | | 630 | | | | | 635 | | | | | 640 |
| Tyr | Val | Pro | Ala | Thr | Ile | Lys | Met | Thr | Val | Glu | Arg | Asp | Gln | Pro | Leu |
| | | | | 645 | | | | | 650 | | | | | 655 | |
| Pro | Thr | Pro | Glu | Leu | Gln | Met | Pro | Thr | Met | Val | Pro | Ser | Tyr | Asp | Leu |
| | | | 660 | | | | | 665 | | | | | 670 | | |
| Gly | Met | Ala | Pro | Asp | Ser | Ser | Met | Ser | Met | Gln | Leu | Gly | Pro | Asp | Met |
| | | 675 | | | | | 680 | | | | | 685 | | | |
| Val | Pro | Gln | Val | Tyr | Pro | Pro | His | Ser | His | Ser | Ile | Pro | Pro | Tyr | Gln |
| | 690 | | | | | 695 | | | | | 700 | | | | |
| Gly | Leu | Ser | Pro | Glu | Glu | Ser | Val | Asn | Val | Leu | Ser | Ala | Phe | Gln | Glu |
| 705 | | | | | 710 | | | | | 715 | | | | | 720 |
| Pro | His | Leu | Gln | Met | Pro | Pro | Ser | Leu | Gly | Gln | Met | Ser | Leu | Pro | Phe |
| | | | | 725 | | | | | 730 | | | | | 735 | |
| Asp | Gln | Pro | His | Pro | Gln | Gly | Leu | Leu | Pro | Cys | Gln | Pro | Gln | Glu | His |
| | | | 740 | | | | | 745 | | | | | 750 | | |
| Ala | Val | Ser | Ser | Pro | Asp | Pro | Leu | Leu | Cys | Ser | Asp | Val | Thr | Met | Val |
| | | 755 | | | | | 760 | | | | | 765 | | | |
| Glu | Asp | Ser | Cys | Leu | Ser | Gln | Pro | Val | Thr | Ala | Phe | Pro | Gln | Gly | Thr |
| | 770 | | | | | 775 | | | | | 780 | | | | |
| Trp | Ile | Gly | Glu | Asp | Ile | Phe | Pro | Pro | Leu | Leu | Pro | Pro | Thr | Glu | Gln |
| 785 | | | | | 790 | | | | | 795 | | | | | 800 |
| Asp | Leu | Thr | Lys | Leu | Leu | Leu | Glu | Gly | Gln | Gly | Glu | Ser | Gly | Gly | Gly |
| | | | | 805 | | | | | 810 | | | | | 815 | |
| Ser | Leu | Gly | Ala | Gln | Pro | Leu | Leu | Gln | Pro | Ser | His | Tyr | Gly | Gln | Ser |
| | | | 820 | | | | | 825 | | | | | 830 | | |
| Gly | Ile | Ser | Met | Ser | His | Met | Asp | Leu | Arg | Ala | Asn | Pro | Ser | Trp | |
| | | 835 | | | | | 840 | | | | | 845 | | | |

( 2 ) INFORMATION FOR SEQ ID NO:3:

( i ) SEQUENCE CHARACTERISTICS:
( A ) LENGTH: 20 base pairs
( B ) TYPE: nucleic acid -continued ( C ) STRANDEDNESS: double
( D ) TOPOLOGY: linear ( i i ) MOLECULE TYPE: cDNA ( x i ) SEQUENCE DESCRIPTION: SEQ ID NO:3:

GTATTTCCCA GAAAAGGAAC 20

( 2 ) INFORMATION FOR SEQ ID NO:4:

( i ) SEQUENCE CHARACTERISTICS:
( A ) LENGTH: 18 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:4:

CTCTTACCTG AGAAATGG 18

( 2 ) INFORMATION FOR SEQ ID NO:5:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:5:

GAATTTCTAA GAAAGGG 17

( 2 ) INFORMATION FOR SEQ ID NO:6:

( i ) SEQUENCE CHARACTERISTICS:
( A ) LENGTH: 16 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:6:

ACATTCACAT GAAGTA 16

( 2 ) INFORMATION FOR SEQ ID NO:7:

( i ) SEQUENCE CHARACTERISTICS:
( A ) LENGTH: 16 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:7:

AACTTCCCAA GAACAG 16

( 2 ) INFORMATION FOR SEQ ID NO:8:

( i ) SEQUENCE CHARACTERISTICS:
( A ) LENGTH: 15 base pairs
( B ) TYPE: nucleic acid
( C ) STRANDEDNESS: double
( D ) TOPOLOGY: linear ( i i ) MOLECULE TYPE: cDNA -continued ( x i ) SEQUENCE DESCRIPTION: SEQ ID NO:8:

AAGGTTTCAG AAGGG 15

( 2 ) INFORMATION FOR SEQ ID NO:9:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:9:

CCTTCCCCTA GCAACAG 17

( 2 ) INFORMATION FOR SEQ ID NO:10:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

Gly Pro Pro Gly Glu Ala Gly Tyr Lys Ala Phe Ser Ser Leu Leu
1 5 10 15

( 2 ) INFORMATION FOR SEQ ID NO:11:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Ala Ser Ser Gly Glu Glu Gly Tyr Lys Pro Phe Gln Asp Leu Ile
1 5 10 15

( 2 ) INFORMATION FOR SEQ ID NO:12:

( i ) SEQUENCE CHARACTERISTICS:
( A ) LENGTH: 740 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Met Ser Gln Trp Tyr Glu Leu Gln Gln Leu Asp Ser Lys Phe Leu Glu
1 5 10 15

Gln Val His Gln Leu Tyr Asp Asp Ser Phe Pro Met Glu Ile Arg Gln
20 25 30

Tyr Leu Ala Gln Trp Leu Glu Lys Gln Asp Trp Glu His Ala Ala Asn
35 40 45

Asp Val Ser Phe Ala Thr Ile Arg Phe His Asp Leu Leu Ser Gln Leu
50 55 60

Asp Asp Gln Tyr Ser Arg Phe Ser Leu Glu Asn Asn Phe Leu Leu Gln
65 70 75 80

His Asn Ile Arg Lys Ser Lys Arg Asn Leu Gln Asp Asn Phe Gln Glu

-continued 85 90 95

Asp Pro Ile Gln Met Ser Met Ile Ile Tyr Ser Cys Leu Lys Glu Glu
100 105 110

Arg Lys Ile Leu Glu Asn Ala Gln Arg Phe Asn Gln Ala Gln Ser Gly
115 120 125

Asn Ile Gln Ser Thr Val Met Leu Asp Lys Gln Lys Glu Leu Asp Ser
130 135 140

Lys Val Arg Asn Val Lys Asp Lys Val Met Cys Ile Glu His Glu Ile
145 150 155 160

Lys Ser Leu Glu Asp Leu Gln Asp Glu Tyr Asp Phe Lys Cys Lys Thr
165 170 175

Leu Gln Asn Arg Glu His Glu Thr Asn Gly Val Ala Lys Ser Asp Gln
180 185 190

Lys Gln Glu Gln Leu Leu Leu Lys Lys Met Tyr Leu Met Leu Asp Asn
195 200 205

Lys Arg Lys Glu Val Val His Lys Ile Ile Glu Leu Leu Asn Val Thr
210 215 220

Glu Leu Thr Gln Asn Ala Leu Ile Asn Asp Glu Leu Val Glu Trp Lys
225 230 235 240

Arg Arg Gln Gln Ser Ala Cys Ile Gly Gly Pro Pro Asn Ala Cys Leu
245 250 255

Asp Gln Leu Gln Gln Val Arg Gln Gln Leu Lys Lys Leu Glu Glu Leu
260 265 270

Glu Gln Lys Tyr Thr Tyr Glu His Asp Pro Ile Thr Lys Asn Lys Gln
275 280 285

Val Leu Trp Asp Arg Thr Phe Ser Leu Phe Gln Gln Leu Ile Gln Ser
290 295 300

Ser Phe Val Val Glu Arg Gln Pro Cys Met Pro Thr His Pro Gln Arg
305 310 315 320

Pro Leu Val Leu Lys Thr Gly Val Gln Phe Thr Val Lys Leu Arg Leu
325 330 335

Leu Val Lys Leu Gln Glu Leu Asn Tyr Asn Leu Lys Val Lys Val Leu
340 345 350

Phe Asp Lys Asp Val Asn Glu Arg Asn Thr Val Lys Gly Phe Arg Lys
355 360 365

Phe Asn Ile Leu Gly Thr His Thr Lys Val Met Asn Met Glu Glu Ser
370 375 380

Thr Asn Gly Ser Leu Ala Ala Glu Phe Arg His Leu Gln Leu Lys Glu
385 390 395 400

Gln Lys Asn Ala Gly Thr Arg Thr Asn Glu Gly Pro Leu Ile Val Thr
405 410 415

Glu Glu Leu His Ser Leu Ser Phe Glu Thr Gln Leu Cys Gln Pro Gly
420 425 430

Leu Val Ile Asp Leu Glu Thr Thr Ser Leu Pro Val Val Val Ile Ser
435 440 445

Asn Val Ser Gln Leu Pro Ser Gly Trp Ala Ser Ile Leu Trp Tyr Asn
450 455 460

Met Leu Val Ala Glu Pro Arg Asn Leu Ser Phe Phe Leu Thr Pro Pro
465 470 475 480

Cys Ala Arg Trp Ala Gln Leu Ser Glu Val Leu Ser Trp Gln Phe Ser
485 490 495

Ser Val Thr Lys Arg Gly Leu Asn Val Asp Gln Leu Asn Met Leu Gly
500 505 510

-continued

Glu Lys Leu Leu Gly Pro Asn Ala Ser Pro Asp Gly Leu Ile Pro Trp
515 520 525

Thr Arg Phe Cys Lys Glu Asn Ile Asn Asp Lys Asn Phe Pro Phe Trp
530 535 540

Leu Trp Ile Glu Ser Ile Leu Glu Leu Ile Lys Lys His Leu Leu Pro
545 550 555 560

Leu Trp Asn Asp Gly Cys Ile Met Gly Phe Ile Ser Lys Glu Arg Glu
565 570 575

Arg Ala Leu Leu Lys Asp Gln Gln Pro Gly Thr Phe Leu Leu Arg Phe
580 585 590

Ser Glu Ser Ser Arg Glu Gly Ala Ile Thr Phe Thr Trp Val Glu Arg
595 600 605

Ser Gln Asn Gly Gly Glu Pro Asp Phe His Ala Val Glu Pro Tyr Thr
610 615 620

Lys Lys Glu Leu Ser Ala Val Thr Phe Pro Asp Ile Ile Arg Asn Tyr
625 630 635 640

Lys Val Met Ala Ala Glu Asn Ile Pro Glu Asn Pro Leu Lys Tyr Leu
645 650 655

Tyr Pro Asn Ile Asp Lys Asp His Ala Phe Gly Lys Tyr Tyr Ser Arg
660 665 670

Pro Lys Glu Ala Pro Glu Pro Met Glu Leu Asp Gly Pro Lys Gly Thr
675 680 685

Gly Tyr Ile Lys Thr Glu Leu Ile Ser Val Ser Glu Val His Pro Ser
690 695 700

Arg Leu Gln Thr Thr Asp Asn Leu Leu Pro Met Ser Pro Glu Glu Phe
705 710 715 720

Asp Glu Val Ser Arg Ile Val Gly Ser Val Glu Phe Asp Ser Met Met
725 730 735

Asn Thr Val Xaa
740

( 2 ) INFORMATION FOR SEQ ID NO:13:

( i ) SEQUENCE CHARACTERISTICS:
( A ) LENGTH: 852 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Met Ala Gln Trp Glu Met Leu Gln Asn Leu Asp Ser Pro Phe Gln Asp
1 5 10 15

Gln Leu His Gln Leu Tyr Ser His Ser Leu Leu Pro Val Asp Ile Arg
20 25 30

Gln Tyr Leu Ala Val Trp Ile Glu Asp Gln Asn Trp Gln Glu Ala Ala
35 40 45

Leu Gly Ser Asp Asp Ser Lys Ala Thr Met Leu Phe Phe His Phe Leu
50 55 60

Asp Gln Leu Asn Tyr Glu Cys Gly Arg Cys Ser Gln Asp Pro Glu Ser
65 70 75 80

Leu Leu Leu Gln His Asn Leu Arg Lys Phe Cys Arg Asp Ile Gln Pro
85 90 95

Phe Ser Gln Asp Pro Thr Gln Leu Ala Glu Met Ile Phe Asn Leu Leu
100 105 110

Leu Glu Glu Lys Arg Ile Leu Ile Gln Ala Gln Arg Ala Gln Leu Glu

-continued

| | | | | | | | | | | | | | | | |
|---|---|---|---|---|---|---|---|---|---|---|---|---|---|---|---|
| | | 115 | | | | | 120 | | | | | 125 | | | |
| Gln | Gly | Glu | Pro | Val | Leu | Glu | Thr | Pro | Val | Glu | Ser | Gln | Gln | His | Glu |
| | 130 | | | | | 135 | | | | | 140 | | | | |
| Ile | Glu | Ser | Arg | Ile | Leu | Asp | Leu | Arg | Ala | Met | Met | Glu | Lys | Leu | Val |
| 145 | | | | | 150 | | | | | 155 | | | | | 160 |
| Lys | Ser | Ile | Ser | Gln | Leu | Lys | Asp | Gln | Gln | Asp | Val | Phe | Cys | Phe | Arg |
| | | | | 165 | | | | | 170 | | | | | 175 | |
| Tyr | Lys | Ile | Gln | Ala | Lys | Gly | Lys | Thr | Pro | Ser | Leu | Asp | Pro | His | Gln |
| | | | 180 | | | | | 185 | | | | | 190 | | |
| Thr | Lys | Glu | Gln | Lys | Ile | Leu | Gln | Glu | Thr | Leu | Asn | Glu | Leu | Asp | Lys |
| | | 195 | | | | | 200 | | | | | 205 | | | |
| Arg | Arg | Lys | Glu | Val | Leu | Asp | Ala | Ser | Lys | Ala | Leu | Leu | Gly | Arg | Leu |
| | 210 | | | | | 215 | | | | | 220 | | | | |
| Thr | Thr | Leu | Ile | Glu | Leu | Leu | Leu | Pro | Lys | Leu | Glu | Glu | Trp | Lys | Ala |
| 225 | | | | | 230 | | | | | 235 | | | | | 240 |
| Gln | Gln | Gln | Lys | Ala | Cys | Ile | Arg | Ala | Pro | Ile | Asp | His | Gly | Leu | Glu |
| | | | | 245 | | | | | 250 | | | | | 255 | |
| Gln | Leu | Glu | Thr | Trp | Phe | Thr | Ala | Gly | Ala | Lys | Leu | Leu | Phe | His | Leu |
| | | | 260 | | | | | 265 | | | | | 270 | | |
| Arg | Gln | Leu | Leu | Lys | Glu | Leu | Lys | Gly | Leu | Ser | Cys | Leu | Val | Ser | Tyr |
| | | 275 | | | | | 280 | | | | | 285 | | | |
| Gln | Asp | Asp | Pro | Leu | Thr | Lys | Gly | Val | Asp | Leu | Arg | Asn | Ala | Gln | Val |
| | 290 | | | | | 295 | | | | | 300 | | | | |
| Thr | Glu | Leu | Leu | Gln | Arg | Leu | Leu | His | Arg | Ala | Phe | Val | Val | Glu | Thr |
| 305 | | | | | 310 | | | | | 315 | | | | | 320 |
| Gln | Pro | Cys | Met | Pro | Gln | Thr | Pro | His | Arg | Pro | Leu | Ile | Leu | Lys | Thr |
| | | | | 325 | | | | | 330 | | | | | 335 | |
| Gly | Ser | Lys | Phe | Thr | Val | Arg | Thr | Arg | Leu | Leu | Val | Arg | Leu | Gln | Glu |
| | | | 340 | | | | | 345 | | | | | 350 | | |
| Gly | Asn | Glu | Ser | Leu | Thr | Val | Glu | Val | Ser | Ile | Asp | Arg | Asn | Pro | Pro |
| | | 355 | | | | | 360 | | | | | 365 | | | |
| Gln | Leu | Gln | Gly | Phe | Arg | Lys | Phe | Asn | Ile | Leu | Thr | Ser | Asn | Gln | Lys |
| | 370 | | | | | 375 | | | | | 380 | | | | |
| Thr | Leu | Thr | Pro | Glu | Lys | Gly | Gln | Ser | Gln | Gly | Leu | Ile | Trp | Asp | Phe |
| 385 | | | | | 390 | | | | | 395 | | | | | 400 |
| Gly | Tyr | Leu | Thr | Leu | Val | Glu | Gln | Arg | Ser | Gly | Gly | Ser | Gly | Lys | Gly |
| | | | | 405 | | | | | 410 | | | | | 415 | |
| Ser | Asn | Lys | Gly | Pro | Leu | Gly | Val | Thr | Glu | Glu | Leu | His | Ile | Ile | Ser |
| | | | 420 | | | | | 425 | | | | | 430 | | |
| Phe | Thr | Val | Lys | Tyr | Thr | Tyr | Gln | Gly | Leu | Lys | Gln | Glu | Leu | Lys | Thr |
| | | 435 | | | | | 440 | | | | | 445 | | | |
| Asp | Thr | Leu | Pro | Val | Val | Ile | Ile | Ser | Asn | Met | Asn | Gln | Leu | Ser | Ile |
| | 450 | | | | | 455 | | | | | 460 | | | | |
| Ala | Trp | Ala | Ser | Val | Leu | Trp | Phe | Asn | Leu | Leu | Ser | Pro | Asn | Leu | Gln |
| 465 | | | | | 470 | | | | | 475 | | | | | 480 |
| Asn | Gln | Gln | Phe | Phe | Ser | Asn | Pro | Pro | Lys | Ala | Pro | Trp | Ser | Leu | Leu |
| | | | | 485 | | | | | 490 | | | | | 495 | |
| Gly | Pro | Ala | Leu | Ser | Trp | Gln | Phe | Ser | Ser | Tyr | Val | Gly | Arg | Gly | Leu |
| | | | 500 | | | | | 505 | | | | | 510 | | |
| Asn | Ser | Asp | Gln | Leu | Ser | Met | Leu | Arg | Asn | Lys | Leu | Phe | Gly | Gln | Asn |
| | | 515 | | | | | 520 | | | | | 525 | | | |
| Cys | Arg | Thr | Glu | Asp | Pro | Leu | Leu | Ser | Trp | Ala | Asp | Phe | Thr | Lys | Arg |
| | 530 | | | | | 535 | | | | | 540 | | | | |

-continued

Glu Ser Pro Pro Gly Lys Leu Pro Phe Trp Thr Trp Leu Asp Lys Ile
545 550 555 560

Leu Glu Leu Val His Asp His Leu Lys Asp Leu Trp Asn Asp Gly Arg
565 570 575

Ile Met Gly Phe Val Ser Arg Ser Gln Glu Arg Arg Leu Leu Lys Lys
580 585 590

Thr Met Ser Gly Thr Phe Leu Leu Arg Phe Ser Glu Ser Ser Glu Gly
595 600 605

Gly Ile Thr Cys Ser Trp Val Glu His Gln Asp Asp Asp Lys Val Leu
610 615 620

Ile Tyr Ser Val Gln Pro Tyr Thr Lys Glu Val Leu Gln Ser Leu Pro
625 630 635 640

Leu Thr Glu Ile Ile Arg His Tyr Gln Leu Leu Thr Glu Glu Asn Ile
645 650 655

Pro Glu Asn Pro Leu Arg Phe Leu Tyr Pro Arg Ile Pro Arg Asp Glu
660 665 670

Ala Phe Gly Cys Tyr Tyr Gln Glu Lys Val Asn Leu Gln Glu Arg Arg
675 680 685

Lys Tyr Leu Lys His Arg Leu Ile Val Val Ser Asn Arg Gln Val Asp
690 695 700

Glu Leu Gln Gln Pro Leu Glu Leu Lys Pro Glu Pro Glu Leu Glu Ser
705 710 715 720

Leu Glu Leu Glu Leu Gly Leu Val Pro Glu Pro Glu Leu Ser Leu Asp
725 730 735

Leu Glu Pro Leu Leu Lys Ala Gly Leu Asp Leu Gly Pro Glu Leu Glu
740 745 750

Ser Val Leu Glu Ser Thr Leu Glu Pro Val Ile Glu Pro Thr Leu Cys
755 760 765

Met Val Ser Gln Thr Val Pro Glu Pro Asp Gln Gly Pro Val Ser Gln
770 775 780

Pro Val Pro Glu Pro Asp Leu Pro Cys Asp Leu Arg His Leu Asn Thr
785 790 795 800

Glu Pro Met Glu Ile Phe Arg Asn Cys Val Lys Ile Glu Glu Ile Met
805 810 815

Pro Asn Gly Asp Pro Leu Leu Ala Gly Gln Asn Thr Val Asp Glu Val
820 825 830

Tyr Val Ser Arg Pro Ser His Phe Tyr Thr Asp Gly Pro Leu Met Pro
835 840 845

Ser Asp Phe Xaa
850

( 2 ) INFORMATION FOR SEQ ID NO:14:

( i ) SEQUENCE CHARACTERISTICS:
( A ) LENGTH: 771 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Met Ala Gln Trp Asn Gln Leu Gln Gln Leu Asp Thr Arg Tyr Leu Glu
1 5 10 15

Gln Leu His Gln Leu Tyr Ser Asp Ser Phe Pro Met Glu Leu Arg Gln
20 25 30

Phe Leu Ala Pro Trp Ile Glu Ser Gln Asp Trp Ala Tyr Ala Ala Ser

-continued 35 40 45

Lys Glu Ser His Ala Thr Leu Val Phe His Asn Leu Leu Gly Glu Ile
50 55 60

Asp Gln Gln Tyr Ser Arg Phe Leu Gln Glu Ser Asn Val Leu Tyr Gln
65 70 75 80

His Asn Leu Arg Arg Ile Lys Gln Phe Leu Gln Ser Arg Tyr Leu Glu
85 90 95

Lys Pro Met Glu Ile Ala Arg Ile Val Ala Arg Cys Leu Trp Glu Glu
100 105 110

Ser Arg Leu Leu Gln Thr Ala Ala Thr Ala Ala Gln Gln Gly Gly Gln
115 120 125

Ala Asn His Pro Thr Ala Ala Val Val Thr Glu Lys Gln Gln Met Leu
130 135 140

Glu Gln His Leu Gln Asp Val Arg Lys Arg Val Gln Asp Leu Glu Gln
145 150 155 160

Lys Met Lys Val Val Glu Asn Leu Gln Asp Asp Phe Asp Phe Asn Tyr
165 170 175

Lys Thr Leu Lys Ser Gln Gly Asp Met Gln Asp Leu Asn Gly Asn Asn
180 185 190

Gln Ser Val Thr Arg Gln Lys Met Gln Gln Leu Glu Gln Met Leu Thr
195 200 205

Ala Leu Asp Gln Met Arg Arg Ser Ile Val Ser Glu Leu Ala Gly Leu
210 215 220

Leu Ser Ala Met Glu Tyr Val Gln Lys Thr Leu Thr Asp Glu Glu Leu
225 230 235 240

Ala Asp Trp Lys Arg Arg Gln Gln Ile Ala Cys Ile Gly Gly Pro Pro
245 250 255

Asn Ile Cys Leu Asp Arg Leu Glu Asn Trp Ile Thr Ser Leu Ala Glu
260 265 270

Ser Gln Leu Gln Thr Arg Gln Gln Ile Lys Lys Leu Glu Glu Leu His
275 280 285

Gln Lys Val Ser Tyr Lys Gly Asp Pro Ile Val Gln His Arg Pro Met
290 295 300

Leu Glu Glu Arg Ile Val Glu Leu Phe Arg Asn Leu Met Lys Ser Ala
305 310 315 320

Phe Val Val Glu Arg Gln Pro Cys Met Pro Met His Pro Asp Arg Pro
325 330 335

Leu Val Ile Lys Thr Gly Val Gln Phe Thr Thr Lys Val Arg Leu Leu
340 345 350

Val Lys Phe Pro Glu Leu Asn Tyr Gln Leu Lys Ile Lys Val Cys Ile
355 360 365

Asp Lys Asp Ser Gly Asp Val Ala Ala Leu Arg Gly Ser Arg Lys Phe
370 375 380

Asn Ile Leu Gly Thr Asn Thr Lys Val Met Asn Met Glu Glu Ser Asn
385 390 395 400

Asn Gly Ser Leu Ser Ala Glu Phe Lys His Leu Thr Leu Arg Glu Gln
405 410 415

Arg Cys Gly Asn Gly Gly Arg Ala Asn Cys Asp Ala Ser Leu Ile Val
420 425 430

Thr Glu Glu Leu His Leu Ile Thr Phe Glu Thr Glu Val Tyr His Gln
435 440 445

Gly Leu Lys Ile Asp Leu Glu Thr His Ser Leu Ser Val Val Val Ile
450 455 460

-continued

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Asn Phe Cys Lys Glu Asn Met Ala Gly Lys Gly Phe Ser
545                 550                 555                 560

Tyr Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Leu Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Ala Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met Xaa
    770

( 2 ) INFORMATION FOR SEQ ID NO:15:

( i ) SEQUENCE CHARACTERISTICS:
( A ) LENGTH: 749 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
            20                  25                  30

Leu Leu Ala Gln Trp Ile Glu Thr Gln Asp Trp Glu Val Ala Ser Asn

-continued 35 40 45

Asn Glu Thr Met Ala Thr Ile Leu Leu Gln Asn Leu Leu Ile Gln Leu
50 55 60

Asp Glu Gln Leu Gly Arg Val Ser Lys Glu Lys Asn Leu Leu Leu Ile
65 70 75 80

His Asn Leu Lys Arg Ile Arg Lys Val Leu Gln Gly Lys Phe His Gly
85 90 95

Asn Pro Met His Val Ala Val Val Ile Ser Asn Cys Leu Arg Glu Glu
100 105 110

Arg Arg Ile Leu Ala Ala Ala Asn Met Pro Ile Gln Gly Pro Leu Glu
115 120 125

Lys Ser Leu Gln Ser Ser Ser Val Ser Glu Arg Gln Arg Asn Val Glu
130 135 140

His Lys Val Ser Ala Ile Lys Asn Ser Val Gln Met Thr Glu Gln Asp
145 150 155 160

Thr Lys Tyr Leu Glu Asp Leu Gln Asp Glu Phe Asp Tyr Arg Tyr Lys
165 170 175

Thr Ile Gln Thr Met Asp Gln Gly Asp Lys Asn Ser Ile Leu Val Asn
180 185 190

Gln Glu Val Leu Thr Leu Leu Gln Glu Met Leu Asn Ser Leu Asp Phe
195 200 205

Lys Arg Lys Glu Ala Leu Ser Lys Met Thr Gln Ile Val Asn Glu Thr
210 215 220

Asp Leu Leu Met Asn Ser Met Leu Leu Glu Glu Leu Gln Asp Trp Lys
225 230 235 240

Lys Arg Gln Gln Ile Ala Cys Ile Gly Gly Pro Leu His Asn Gly Leu
245 250 255

Asp Gln Leu Gln Asn Cys Phe Thr Leu Leu Ala Glu Ser Leu Phe Gln
260 265 270

Leu Arg Gln Gln Leu Glu Lys Leu Gln Glu Gln Ser Thr Lys Met Thr
275 280 285

Tyr Glu Gly Asp Pro Ile Pro Ala Gln Arg Ala His Leu Leu Glu Arg
290 295 300

Ala Thr Phe Leu Ile Tyr Asn Leu Phe Lys Asn Ser Phe Val Val Glu
305 310 315 320

Arg Gln Pro Cys Met Pro Thr His Pro Gln Arg Pro Met Val Leu Lys
325 330 335

Thr Leu Ile Gln Phe Thr Val Lys Leu Arg Leu Leu Ile Lys Leu Pro
340 345 350

Glu Leu Asn Tyr Gln Val Lys Val Lys Ala Ser Ile Asp Lys Asn Val
355 360 365

Ser Thr Leu Ser Asn Arg Arg Phe Val Leu Cys Gly Thr His Val Lys
370 375 380

Ala Met Ser Ser Glu Glu Ser Ser Asn Gly Ser Leu Ser Val Glu Phe
385 390 395 400

Arg His Leu Gln Pro Lys Glu Met Lys Cys Ser Thr Gly Ser Lys Gly
405 410 415

Asn Glu Gly Cys His Met Val Thr Glu Glu Leu His Ser Ile Thr Phe
420 425 430

Glu Thr Gln Ile Cys Leu Tyr Gly Leu Thr Ile Asn Leu Glu Thr Ser
435 440 445

Ser Leu Pro Val Val Met Ile Ser Asn Val Ser Gln Leu Pro Asn Ala
450 455 460

-continued

Trp Ala Ser Ile Ile Trp Tyr Asn Val Ser Thr Asn Asp Ser Gln Asn
465 470 475 480

Leu Val Phe Phe Asn Asn Pro Pro Ser Val Thr Leu Gly Gln Leu Leu
485 490 495

Glu Val Met Ser Trp Gln Phe Ser Ser Tyr Val Gly Arg Gly Leu Asn
500 505 510

Ser Glu Gln Leu Asn Met Leu Ala Glu Lys Leu Thr Val Gln Ser Asn
515 520 525

Tyr Asn Asp Gly His Leu Thr Trp Ala Lys Phe Cys Lys Glu His Leu
530 535 540

Pro Gly Lys Thr Phe Thr Phe Trp Thr Trp Leu Glu Ala Ile Leu Asp
545 550 555 560

Leu Ile Lys Lys His Ile Leu Pro Leu Trp Ile Asp Gly Tyr Ile Met
565 570 575

Gly Phe Val Ser Lys Glu Lys Glu Arg Leu Leu Leu Lys Asp Lys Met
580 585 590

Pro Gly Thr Phe Leu Leu Arg Phe Ser Glu Ser His Leu Gly Gly Ile
595 600 605

Thr Phe Thr Trp Val Asp Gln Ser Glu Asn Gly Glu Val Arg Phe His
610 615 620

Ser Val Glu Pro Tyr Asn Lys Gly Arg Leu Ser Ala Leu Ala Phe Ala
625 630 635 640

Asp Ile Leu Arg Asp Tyr Lys Val Ile Met Ala Glu Asn Ile Pro Glu
645 650 655

Asn Pro Leu Lys Tyr Leu Tyr Pro Asp Ile Pro Lys Asp Lys Ala Phe
660 665 670

Gly Lys His Tyr Ser Ser Gln Pro Cys Glu Val Ser Arg Pro Thr Glu
675 680 685

Arg Gly Asp Lys Gly Tyr Val Pro Ser Val Phe Ile Pro Ile Ser Thr
690 695 700

Ile Arg Ser Asp Ser Thr Glu Pro Gln Ser Pro Ser Asp Leu Leu Pro
705 710 715 720

Met Ser Pro Ser Ala Tyr Ala Val Leu Arg Glu Asn Leu Ser Pro Thr
725 730 735

Thr Ile Glu Thr Ala Met Asn Ser Pro Tyr Ser Ala Glu
740 745

( 2 ) INFORMATION FOR SEQ ID NO:16:

( i ) SEQUENCE CHARACTERISTICS:
( A ) LENGTH: 734 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

Met Ala Gly Trp Ile Gln Ala Gln Gln Leu Gln Gly Asp Ala Leu Arg
1 5 10 15

Gln Met Gln Val Leu Tyr Gly Gln His Phe Pro Ile Glu Val Arg His
20 25 30

Tyr Leu Ala Gln Trp Ile Glu Ser Gln Pro Trp Asp Ala Ile Asp Leu
35 40 45

Asp Asn Pro Gln Asp Arg Ala Gln Val Thr Gln Leu Leu Glu Gly Leu
50 55 60

Val Gln Glu Leu Gln Lys Lys Ala Glu His Gln Val Gly Glu Asp Gly

-continued 65 70 75 80

Phe Leu Leu Lys Ile Lys Leu Gly His Tyr Val His Val Ser Ser Arg
85 90 95

Thr Arg Thr Thr Ala Ala Pro Trp Ser Trp Leu Arg Cys Ile Arg His
100 105 110

Ile Leu Tyr Asn Glu Gln Arg Leu Val Arg Glu Ala Thr Asn Gly Asn
115 120 125

Ser Ser Ala Gly Ile Leu Val Asp Ala Met Ser Gln Lys His Leu Gln
130 135 140

Ile Asn Gln Thr Phe Glu Glu Leu Arg Leu Val Thr Gln Asp Thr Glu
145 150 155 160

Asn Glu Leu Lys Lys Leu Gln Gln Thr Gln Glu Tyr Phe Ile Ile Gln
165 170 175

Tyr Gln Glu Ser Leu Arg Ile Gln Ala Gln Phe Ala Gln Leu Ala Gln
180 185 190

Leu Asn Pro Gln Glu Arg Leu Ser Arg Glu Thr Ala Leu Gln Gln Lys
195 200 205

Gln Val Ser Leu Glu Ala Trp Leu Gln Arg Glu Ala Gln Thr Leu Gln
210 215 220

Gln Tyr Arg Val Glu Leu Ala Glu Lys His Gln Lys Thr Leu Gln Leu
225 230 235 240

Leu Arg Lys Gln Gln Thr Ile Ile Leu Asp Asp Glu Leu Ile Gln Trp
245 250 255

Lys Arg Arg His Asp Trp Arg Gly Met Glu Ala Pro Pro Arg Ser Leu
260 265 270

Asp Val Leu Gln Ser Trp Cys Glu Lys Leu Ala Glu Ile Ile Trp Gln
275 280 285

Asn Arg Gln Gln Ile Arg Arg Ala Glu His Leu Cys Gln Gln Leu Pro
290 295 300

Ile Pro Gly Pro Val Glu Glu Met Leu Ala Glu Val Asn Ala Thr Ile
305 310 315 320

Thr Asp Ile Ile Ser Ala Leu Val Thr Ser Thr Phe Ile Ile Glu Lys
325 330 335

Gln Pro Pro Gln Val Leu Lys Thr Gln Thr Lys Phe Ala Ala Thr Val
340 345 350

Arg Leu Leu Val Gly Gly Lys Leu Asn Val His Met Asn Pro Pro Gln
355 360 365

Val Lys Ala Thr Ile Ile Ser Glu Gln Gln Ala Lys Ser Leu Leu Lys
370 375 380

Asn Glu Asn Thr Arg Asn Glu Cys Ser Gly Glu Ile Leu Asn Asn Cys
385 390 395 400

Cys Val Met Glu Tyr His Gln Arg Thr Gly Thr Leu Ser Ala His Phe
405 410 415

Arg Asn Met Ser Leu Lys Arg Ile Lys Arg Ala Asp Arg Arg Gly Ala
420 425 430

Glu Ser Val Thr Glu Glu Lys Phe Thr Val Leu Phe Glu Ser Gln Phe
435 440 445

Ser Val Gly Ser Asn Glu Leu Val Phe Gln Val Lys Thr Leu Ser Leu
450 455 460

Pro Val Val Val Ile Val His Gly Ser Gln Asp His Asn Ala Thr Ala
465 470 475 480

Thr Val Leu Trp Asp Asn Ala Phe Ala Glu Pro Gly Arg Val Pro Phe
485 490 495

-continued

Ala Val Pro Asp Lys Val Leu Trp Pro Gln Leu Cys Glu Ala Leu Asn
500 505 510

Met Lys Phe Lys Ala Glu Val Gln Ser Asn Arg Gly Leu Thr Lys Glu
515 520 525

Asn Leu Leu Phe Leu Ala Gln Lys Leu Phe Asn Asn Ser Ser Ser His
530 535 540

Leu Glu Asp Tyr Asn Gly Met Ser Val Ser Trp Ser Gln Phe Asn Arg
545 550 555 560

Glu Asn Leu Pro Gly Trp Asn Tyr Thr Phe Trp Gln Trp Phe Asp Gly
565 570 575

Val Met Glu Val Leu Lys Lys His His Lys Pro His Trp Asn Asp Gly
580 585 590

Ala Ile Leu Gly Phe Val Asn Lys Gln Gln Ala His Asp Leu Leu Ile
595 600 605

Asn Lys Pro Asp Gly Thr Phe Leu Leu Arg Phe Ser Asp Ser Glu Ile
610 615 620

Gly Gly Ile Thr Ile Ala Trp Lys Phe Asp Ser Pro Asp Arg Asn Leu
625 630 635 640

Trp Asn Leu Lys Pro Phe Thr Thr Arg Glu Gly Ser Ile Arg Ser Leu
645 650 655

Ala Asp Arg Leu Gly Asp Leu Asn Tyr Leu Ile Tyr Val Phe Pro Asp
660 665 670

Arg Pro Lys Asp Glu Val Phe Ser Lys Tyr Tyr Thr Pro Val Leu Ala
675 680 685

Lys Ala Val Asp Gly Tyr Val Lys Pro Gln Ile Lys Gln Val Val Pro
690 695 700

Glu Phe Val Ser Ala Ser Ala Asp Ser Ala Gly Ser Arg His Leu His
705 710 715 720

Gly Pro Gly Ser Leu Pro Ser Arg Val Pro Pro Ala Ser Leu
725 730

( 2 ) INFORMATION FOR SEQ ID NO:17:

( i ) SEQUENCE CHARACTERISTICS:
( A ) LENGTH: 263 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

Met Gln Trp Gln Gln Leu Leu Gln Gln Leu Tyr Asp Phe Pro Glu Arg
1 5 10 15

Leu Ala Trp Ile Glu Gln Trp Ala Ala Thr Leu Leu Leu Leu Arg Glu
20 25 30

Leu His Asn Gln Pro Ile Leu Glu Glu Arg Leu Ala Gln Gln Lys Gln
35 40 45

Asp Lys Leu Leu Asp Arg Glu Leu Leu Glu Leu Trp Lys Arg Arg Gln
50 55 60

Gln Ala Cys Ile Gly Pro Leu Asp Leu Gln Leu Ala Leu Tyr Asp Pro
65 70 75 80

Leu Arg Leu Leu Ser Phe Val Val Glu Gln Pro Cys Met Pro Pro Arg
85 90 95

Pro Lys Thr Gly Val Phe Thr Val Arg Leu Leu Glu Asn Lys Asp Lys
100 105 110

Leu Gly Arg Phe Asn Lys Glu Leu Phe His Leu Glu Lys Val Thr Glu

-continued

| | | | | | | | | | | | | | | | |
|---|---|---|---|---|---|---|---|---|---|---|---|---|---|---|---|
| | | 115 | | | | | 120 | | | | | 125 | | | |
| Glu | Leu | His | Phe | Gly | Leu | Ile | Leu | Thr | Ser | Leu | Pro | Val | Val | Val | Ile |
| | 130 | | | | | 135 | | | | | 140 | | | | |
| Ser | Asn | Gln | Asn | Ala | Trp | Ala | Ser | Ile | Leu | Trp | Asn | Asn | Phe | Phe | Pro |
| 145 | | | | | 150 | | | | | 155 | | | | | 160 |
| Pro | Trp | Gln | Leu | Glu | Leu | Ser | Trp | Gln | Phe | Ser | Ser | Val | Arg | Gly | Leu |
| | | | | 165 | | | | | 170 | | | | | 175 | |
| Glu | Gln | Leu | Leu | Ala | Lys | Leu | Trp | Phe | Lys | Glu | Gly | Phe | Phe | Trp | Trp |
| | | | 180 | | | | | 185 | | | | | 190 | | |
| Asp | Ile | Leu | Leu | Lys | Lys | His | Leu | Trp | Asn | Asp | Gly | Ile | Met | Gly | Pro |
| | | 195 | | | | | 200 | | | | | 205 | | | |
| Ser | Lys | Glu | Arg | Leu | Leu | Gly | Thr | Phe | Leu | Leu | Arg | Phe | Ser | Glu | Ser |
| | 210 | | | | | 215 | | | | | 220 | | | | |
| Gly | Gly | Ile | Thr | Trp | Val | Val | Pro | Tyr | Thr | Lys | Leu | Ser | Asp | Ile | Ile |
| 225 | | | | | 230 | | | | | 235 | | | | | 240 |
| Arg | Tyr | Asn | Ile | Pro | Pro | Leu | Leu | Tyr | Pro | Ile | Lys | Ala | Phe | Gly | Lys |
| | | | | 245 | | | | | 250 | | | | | 255 | |
| Glu | Glu | Leu | Pro | Leu | Pro | Ser | | | | | | | | | |
| | | | 260 | | | | | | | | | | | | |